(12) United States Patent
Eisenschmid et al.

(10) Patent No.: US 7,863,487 B2
(45) Date of Patent: Jan. 4, 2011

(54) HYDROFORMYLATION PROCESS WITH IMPROVED CONTROL OVER PRODUCT ISOMERS

(75) Inventors: Thomas C. Eisenschmid, Cross Lanes, WV (US); Glenn A. Miller, South Charleston, WV (US); Ronald R. Peterson, St. Albans, WV (US); Anthony G. Abatjoglon, Charleston, WV (US)

(73) Assignee: Dow Technology Investments LLC

( * ) Notice: Subject to any disclaimer, the term of this patent is extended or adjusted under 35 U.S.C. 154(b) by 24 days.

(21) Appl. No.: 12/530,889

(22) PCT Filed: Mar. 12, 2008

(86) PCT No.: PCT/US2008/056602

§ 371 (c)(1),
(2), (4) Date: Nov. 18, 2009

(87) PCT Pub. No.: WO2008/115740

PCT Pub. Date: Sep. 25, 2008

(65) Prior Publication Data

US 2010/0069680 A1    Mar. 18, 2010

Related U.S. Application Data

(60) Provisional application No. 60/918,998, filed on Mar. 20, 2007.

(51) Int. Cl.
*C07C 45/50*    (2006.01)
(52) U.S. Cl. ...................................... 568/454
(58) Field of Classification Search ................ 568/454
See application file for complete search history.

(56) References Cited

U.S. PATENT DOCUMENTS

| | | | |
|---|---|---|---|
| 3,415,906 A | 12/1968 | Shepard et al. | |
| 3,527,809 A | 9/1970 | Pruett et al. | |
| 4,148,830 A | 4/1979 | Pruett et al. | |
| 4,518,809 A | 5/1985 | Foster et al. | |
| 4,528,403 A | 7/1985 | Tano et al. | |
| 4,567,302 A | 1/1986 | Sivaramakrishnan | |
| 4,567,306 A | 1/1986 | Dennis et al. | |
| 4,593,127 A | 6/1986 | Bunning et al. | |
| 4,599,206 A | 7/1986 | Billig et al. | |
| 4,668,651 A | 5/1987 | Billig et al. | |
| 4,717,775 A | 1/1988 | Billig et al. | |
| 4,748,261 A | 5/1988 | Billig et al. | |
| 4,769,498 A | 9/1988 | Billig et al. | |
| 4,774,361 A | 9/1988 | Maher et al. | |
| 4,885,401 A | 12/1989 | Billig et al. | |
| 4,935,299 A | 6/1990 | Yamaguchi et al. | |
| 5,059,710 A | 10/1991 | Abatjoglou et al. | |
| 5,102,505 A | 4/1992 | Sorensen | |
| 5,110,990 A | 5/1992 | Blessing et al. | |
| 5,113,022 A | 5/1992 | Abatjoglou et al. | |
| 5,114,473 A | 5/1992 | Abatjoglou et al. | |
| 5,179,055 A | 1/1993 | Wink et al. | |
| 5,202,297 A | 4/1993 | Lorz et al. | |
| 5,233,093 A | 8/1993 | Pitchai et al. | |
| 5,235,113 A | 8/1993 | Sato et al. | |
| 5,254,741 A | 10/1993 | Lorz et al. | |
| 5,264,616 A | 11/1993 | Roeper et al. | |
| 5,288,918 A | 2/1994 | Maher et al. | |
| 5,312,996 A | 5/1994 | Packett | |
| 5,364,950 A | 11/1994 | Babin et al. | |
| 5,449,653 A | 9/1995 | Briggs et al. | |
| 5,506,273 A | 4/1996 | Haruta et al. | |
| 5,741,945 A * | 4/1998 | Bryant et al. | 568/454 |
| 5,763,679 A * | 6/1998 | Nicholson et al. | 568/454 |
| 5,874,639 A | 2/1999 | Nicholson et al. | |
| 5,874,640 A | 2/1999 | Bryant et al. | |
| 5,892,119 A | 4/1999 | Bryant et al. | |
| 5,932,772 A | 8/1999 | Argyropoulos et al. | |
| 5,952,530 A | 9/1999 | Argyropoulos et al. | |
| 5,965,754 A | 10/1999 | Clark et al. | |
| 6,031,116 A | 2/2000 | Bowman et al. | |
| 6,090,987 A | 7/2000 | Billig et al. | |
| 6,255,499 B1 | 7/2001 | Kuperman et al. | |

(Continued)

FOREIGN PATENT DOCUMENTS

WO    WO2005120705 A1 * 12/2005

OTHER PUBLICATIONS

Billig et al., "Oxo Process", Kirk-Othmer, Encyclopedia of Chemical Technology, 4th Edition, 1996, p. 909-919.

*Primary Examiner*—Sikarl A Witherspoon
(74) *Attorney, Agent, or Firm*—Marie F. Zukerman; Paul D. Hayhurst

(57) ABSTRACT

A continuous hydroformylation process for producing a mixture of aldehydes with improved flexibility and stability of a normal/branched (N/I) isomer ratio of the product aldehydes. The process involves reacting one or more olefinically-unsaturated compounds with carbon monoxide and hydrogen in the presence of an organopolyphosphite ligand and an organomonophosphite ligand, at least one of such ligands being bonded to a transition metal to form a transition metal-ligand complex hydroformylation catalyst; the process being conducted at a sub-stoichiometric molar ratio of organopolyphosphite ligand to transition metal, at a super-stoichiometric (>2/1) molar ratio of organomonophosphite ligand to transition metal, and at a carbon monoxide partial pressure in the inverse order region of the hydroformylation rate curve; and controlling and varying the isomer ratio by varying the concentration of organopolyphosphite ligand relative to transition metal.

20 Claims, 2 Drawing Sheets

U.S. PATENT DOCUMENTS

| | | |
|---|---|---|
| 6,294,700 B1 | 9/2001 | Kanel et al. |
| 6,303,829 B1 | 10/2001 | Kanel et al. |
| 6,303,830 B1 | 10/2001 | Argyropoulos et al. |
| 6,307,109 B1 | 10/2001 | Kanel et al. |
| 6,307,110 B1 | 10/2001 | Argyropoulos et al. |
| 7,446,231 B2 | 11/2008 | Peterson et al. |
| 2007/0123735 A1 | 5/2007 | Jeon et al. |
| 2008/0281128 A1 | 11/2008 | Karvinen et al. |

* cited by examiner

HYDROFORMYLATION PROCESS WITH IMPROVED CONTROL OVER PRODUCT ISOMERS

CROSS-REFERENCE TO RELATED APPLICATIONS

This application is a 371 of PCT/US2008/056602 filed Mar. 12, 2008, which claims the benefit of U.S. Provisional Application Ser. No. 60/918,998, filed on Mar. 20, 2007.

BACKGROUND OF THE INVENTION

This invention pertains to an improved process for hydroformylating an olefinically-unsaturated compound to produce a mixture of aldehyde products.

It is well known in the art that one or more aldehyde products can be produced by contacting under reaction conditions an olefinically-unsaturated compound with carbon monoxide and hydrogen in the presence of a metal-organophosphorus ligand complex catalyst. One such process, as exemplified in U.S. Pat. Nos. 4,148,830, 4,717,775, and U.S. Pat. No. 4,769,498, involves continuous hydroformylation with recycle of a solution containing the metal-organophosphorus ligand complex catalyst, more preferably, a Group VIII-organophosphorus ligand complex catalyst. Rhodium is a preferred Group VIII metal. Organophosphines and organopolyphosphites are preferred organophosphorus ligands. Aldehydes produced by hydroformylation processes have a wide range of utility, for example, as intermediates for hydrogenation to aliphatic alcohols, for amination to aliphatic amines, for oxidation to aliphatic acids, and for aldol condensation to produce plasticizers.

Until recently, the art disclosed that a high normal to branched (normal/branched or N/I) isomer ratio of the product aldehydes was desirable; however, with present day market demands for specialty chemicals, a low N/I isomer ratio may also be desirable. For the purposes of this invention, a "high" N/I isomer ratio refers to an isomer ratio equal to or greater than 10/1; while a "low" N/I isomer ratio refers to an isomer ratio less than 10/1. Up to the present time, no single catalyst has been capable of producing a wider range of N/I isomer ratios beyond the inherent ratios achievable by the single catalyst itself.

Rhodium-organophosphine ligand complex catalysts, such as rhodium-triphenylphosphine ligand complex catalysts, are known to produce a limited N/I isomer ratio from about 5/1 to about 12/1. To obtain an N/I isomer ratio outside this range, the rhodium-organophosphine ligand complex catalyst must be replaced with another complex catalyst capable of achieving the desired ratio. Converting a manufacturing site from one catalyst to another is costly and non-productive. Additionally, the activity of a rhodium-organophosphine ligand complex catalyst is undesirably low; and thus, the concentration of catalyst including costly rhodium metal required to obtain acceptable process productivity is undesirably high. Moreover, the organophosphine ligand is required to be provided at greater than 200/1 mole-equivalents per mole-equivalent of rhodium.

As an alternative, metal-organopolyphosphite ligand complex catalysts have been shown to provide higher activity and higher N/I isomer ratios in hydroformylation processes, as compared with metal-organophosphine ligand complex catalysts. Higher activity beneficially allows for reduction in the concentration of catalyst, hence expensive metal (e.g., Rh), in hydroformylation reaction fluids. Moreover, the requirement for excess ligand is also reduced. Nevertheless, the N/I isomer ratio obtained from metal-organopolyphosphite ligand complex catalysts is still limited to a narrow range and not sufficiently flexible to meet current day market demands, which range from about 2/1 to 75/1 or higher. More significantly, stabilization of the organopolyphosphite ligand causes concern, because this ligand is hydrolytically unstable, particularly, at low carbon monoxide partial pressures. The art discloses, as shown in U.S. Pat. No. 5,763,679 and WO/2006/020287, that hydrolytic deactivation of metal-organopolyphosphite ligand complex catalysts can be reversed or reduced by conducting the hydroformylation process in a reaction region where the hydroformylation reaction rate is negative or inverse order in carbon monoxide. As used herein, a hydroformylation reaction rate that is "negative or inverse order in carbon monoxide" refers to a region wherein the hydroformylation reaction rate increases as carbon monoxide partial pressure decreases, and wherein the hydroformylation reaction rate decreases as carbon monoxide partial pressure increases.

Typically, the N/I isomer ratio varies inversely with carbon monoxide partial pressure; thus, the ratio decreases as carbon monoxide partial pressure increases, and the ratio increases as carbon monoxide partial pressure decreases. Controlling the N/I isomer ratio via carbon monoxide partial pressure creates problems, however. At low-end carbon monoxide partial pressures (about <15 psi or <103 kPa), hydrogenation of the reactant olefin may increase with efficiency losses to by-product alkanes. At high end carbon monoxide partial pressures (about >50 psi or >345 kPa) overall catalyst activity is reduced and the rate of catalyst deactivation is increased. Thus, the optimal range of carbon monoxide partial pressure, within the negative order regime, imposes restrictions on the N/I isomer ratios achievable.

Prior art, exemplified by U.S. Pat. No. 5,741,945, disclose a hydroformylation process employing a mixture of an organopolyphosphite ligand and a sterically-hindered organophosphorus ligand selected from organophosphine ligands, organomonophosphite ligands, and organomonophosphite-monophosphate ligands. This art illustrates hydroformylation in batch processes wherein an incremental addition of organopolyphosphite ligand may produce a "step-ladder" discontinuity in the N/I product isomer ratio. Moreover, the applicants of the present invention have found that in such processes, the N/I isomer ratio varies over days and weeks and cannot be sufficiently controlled.

Other art, exemplified by WO-A1-2006/098685 and U.S. Pat. No. 5,233,093, teach hydroformylations in batch processes in the presence of mixtures of organophosphine ligands. The references are silent with regard to controlling the N/I isomer ratio over an extended period of time, namely, days or weeks.

WO-A1-2005/120705 discloses a hydroformylation process in the presence of a transition metal and a mixture of a monophosphite ligand and a bisphosphite ligand containing terminal alkoxy groups. The N/I selectivity of the aldehyde product produced is determined by manipulating the mixture of ligands relative to the transition metal. No representation is made of the stability or time dependency of the N/I ratio.

Accordingly, a need exists for a hydroformylation process having improved flexibility over a wider range of N/I isomer ratios as well as improved N/I stability with time. To the extent possible, such a process should not depend upon varying carbon monoxide partial pressure. Moreover, such a process should provide for acceptable catalyst activity, reduce transition metal usage, and reduce undesirable by-product formation.

SUMMARY OF THE INVENTION

This invention provides for a hydroformylation process for continuous production of a mixture of aldehyde products with improved control over a normal/branched (N/I) isomer ratio of the product aldehydes, as evidenced by expanded flexibility and stability of the N/I isomer ratio. The process of this invention comprises contacting under continuous reaction conditions in a hydroformylation reaction fluid, one or more olefinically-unsaturated compounds, carbon monoxide, and hydrogen in the presence of a mixture of an organopolyphosphite ligand and an organomonophosphite ligand, at least one of said ligands being bonded to a transition metal to form a transition metal-ligand complex hydroformylation catalyst. The organopolyphosphite ligand comprises a plurality of phosphorus (III) atoms each bonded to three hydrocarbyloxy radicals, any non-bridging species of which consists essentially of an aryloxy radical (substituted or unsubstituted). The contacting is further conducted:

(a) at a sub-stoichiometric molar ratio of organopolyphosphite ligand to transition metal such that said molar ratio is greater than 0 but less than 1.0/1;

(b) at a super-stoichiometric molar ratio of organomonophosphite ligand to transition metal such that said molar ratio is greater than 2/1;

(c) at a carbon monoxide partial pressure in a negative order region of a hydroformylation rate curve wherein rate of reaction decreases as carbon monoxide partial pressure increases, and wherein rate of reaction increases as carbon monoxide partial pressure decreases, the rate curve being measured on an identical hydroformylation process in the presence of the organopolyphosphite ligand but not the organomonophosphite ligand; and (d) varying the molar ratio of organopolyphosphite ligand to transition metal within the aforementioned sub-stoichiometric range while maintaining the molar ratio of organomonophosphite ligand to transition metal in the aforementioned super-stoichiometric range, so as to control continuously the normal/branched isomer ratio of the aldehyde products.

The hydroformylation process of this invention provides several advantages over prior art hydroformylation processes, although the statement herein of such advantages is not meant to limit the claimed invention in any manner. As a first advantage, the process of this invention allows for continuous operation of a hydroformylation process with stable N/I isomer ratio over an extended reaction time, on the order of weeks or months, as desired. Secondly, the N/I isomer ratio of the aldehyde products can be varied over a wider range than heretofore possible. Such N/I isomer control is achieved without varying carbon monoxide partial pressure, and consequently, avoids problems associated with working at low end and high end carbon monoxide partial pressures. The process can be operated at an optimal carbon monoxide partial pressure in the negative order region of the hydroformylation rate curve, while still achieving an expanded N/I isomer ratio. An N/I isomer ratio can be achieved within a broad range from about 1/1 to about 100/1, preferably, from about 2/1 to about 75/1; but the exact range achievable depends upon the olefin and ligand pair selected. In preferred embodiments of this invention, variation in the N/I isomer ratio is continuous without a "step-ladder" discontinuity.

The above-described advantages simplify operation at a manufacturing site when market demands change focus and an N/I isomer ratio different from the current production is desired. Production need not be stopped for conversion of the site to a new catalyst. Rather, the N/I isomer ratio can be varied with one organopolyphosphite-organomonophosphite mixed ligand system merely by varying the concentration of the organopolyphosphite ligand relative to transition metal. The present invention also allows for advantageous "drop-in" retrofitting of older triphenylphosphine-based hydroformylation plants with the organopolyphosphite-organomonophosphite mixed ligand system of the present invention. In this regard, the present invention provides for operation at lower metal and ligand concentrations while retaining acceptable productivity, as compared with triphenylphosphine-based plants.

DRAWINGS

DETAILED DESCRIPTION OF THE INVENTION

Figure 1:
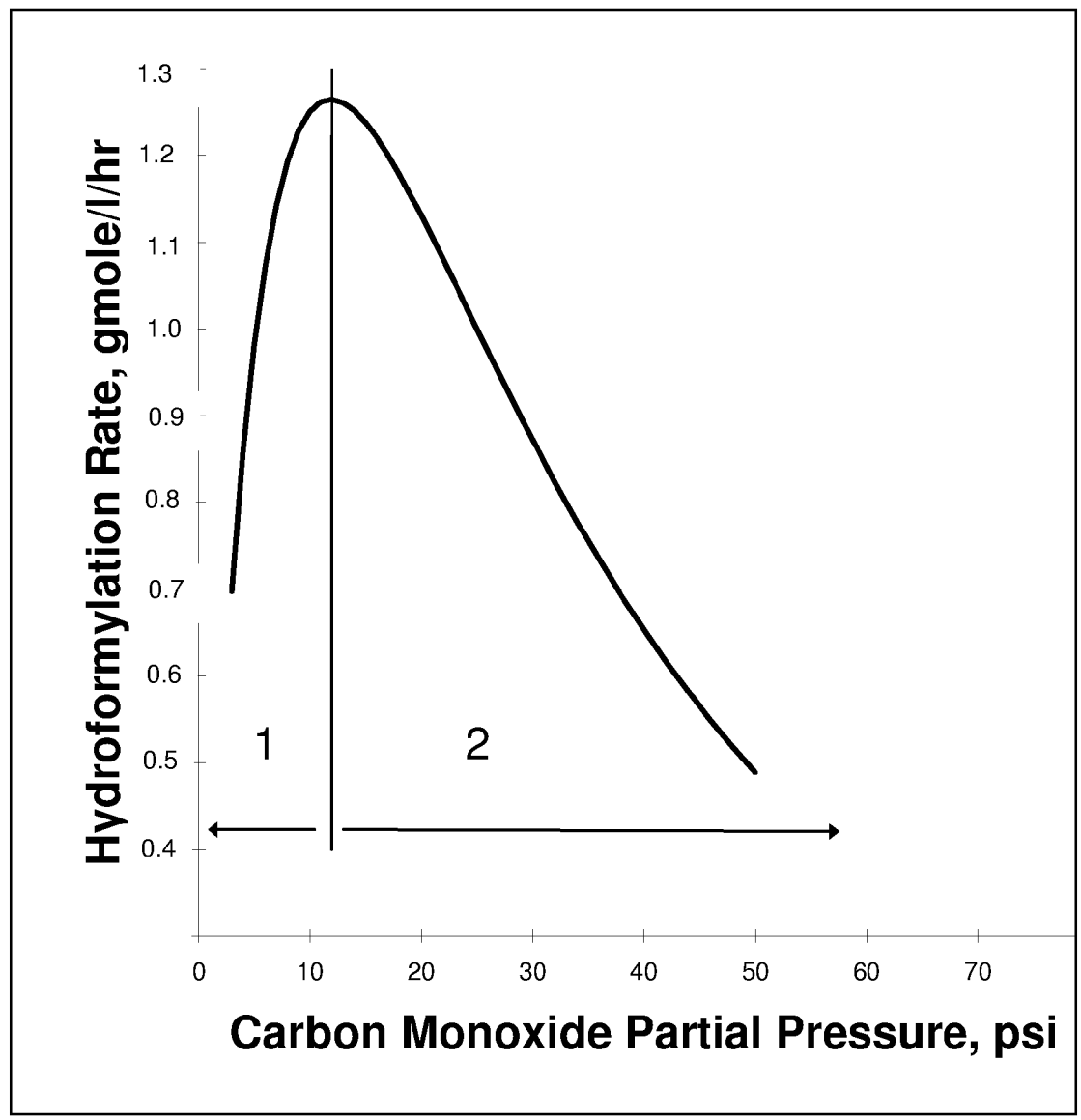
FIG. 1 illustrates a plot of hydroformylation reaction rate, given in units of gram-moles of aldehyde produced per liter reaction fluid per hour versus carbon monoxide partial pressure. The positive (1) and negative (2) order regions of the rate curve are labeled.

The invention described herein provides for a hydroformylation process for producing a mixture of aldehydes, the process further providing for improved control over the normal/branched (N/I) isomer ratio of the aldehyde products, as compared with prior art hydroformylation processes. In this invention, improved control is expressed in an expanded N/I ratio and improved N/I stability over time. As described in detail hereinafter, the process of this invention comprises contacting under continuous reaction conditions in a hydroformylation reaction fluid, one or more olefinically-unsaturated compounds, carbon monoxide, and hydrogen in the presence of a mixture of an organopolyphosphite ligand and an organomonophosphite ligand, at least one of said ligands being bonded to a transition metal to form a transition metal-ligand complex hydroformylation catalyst. The organopolyphosphite ligand comprises a plurality of phosphorus (III) atoms each bonded to three hydrocarbyloxy radicals, any non-bridging species of which consists essentially of a substituted or unsubstituted aryloxy radical. The contacting is further conducted:

(a) at a sub-stoichiometric molar ratio of organopolyphosphite ligand to transition metal such that said molar ratio is greater than 0 but less than 1.0/1;

(b) at a super-stoichiometric molar ratio of organomonophosphite ligand to transition metal such that said molar ratio is greater than 2/1;

(c) at a carbon monoxide partial pressure in a negative order region of a hydroformylation rate curve wherein rate of reaction decreases as carbon monoxide partial pressure increases, and wherein rate of reaction increases as carbon monoxide partial pressure decreases, the rate curve being based on an identical hydroformylation process in the presence of the organopolyphosphite ligand but not the organomonophosphite ligand; and (d) varying the molar ratio of organopolyphosphite ligand to transition metal within the aforementioned sub-stoichiometric range while maintaining the molar ratio of organomonophosphite ligand to transition metal in the aforementioned super-stoichiometric range, so as to control continuously the normal/branched isomer ratio of the aldehyde products.

In a preferred embodiment of the claimed process, the N/I isomer ratio may vary continuously within a range from about 1/1 to about 100/1, depending upon the particular ligand pair selected. More preferably, the N/I isomer ratio varies from greater than about 2/1 to less than about 75/1, more preferably, less than about 50/1.

In another preferred embodiment of this invention, when the concentration of organopolyphosphite ligand is increased, the N/I isomer ratio of aldehyde products increases; and when the concentration of organopolyphosphite ligand is decreased, the N/I isomer ratio of aldehyde products decreases.

In another preferred embodiment of this invention, the concentration of organopolyphosphite ligand in the hydroformylation reaction fluid is decreased by addition of water to the hydroformylation process with consequential hydrolytic degradation of the organopolyphosphite ligand. The degree to which the concentration of organopolyphosphite ligand is decreased through hydrolytic degradation depends upon the quantity of water added to the hydroformylation reaction fluid and the acidity or basicity of the hydroformylation reaction fluid, which can be controlled by additives, such as weak acids or bases or buffers, or controlled by the conditions within a downstream extractor.

In another preferred embodiment of this invention, the quantity of organopolyphosphite ligand is decreased by addition of an oxidant to the hydroformylation process with consequential oxidative degradation of the organopolyphosphite ligand. A common oxidative degradation converts a phosphite group to a phosphate group; but any conversion of P(III) to P(V) qualifies as an oxidative degradation. The degree to which the concentration of organopolyphosphite ligand is decreased through oxidative degradation depends upon the quantity of oxidant added to the hydroformylation reaction fluid.

In a more preferred embodiment, the organopolyphosphite ligand is 6,6'-[[3,3',5,5'-tetrakis(1,1-dimethylethyl)-[1,1'-biphenyl]-2,2'-diyl]bis(oxy)]bis-dibenzo[d,f][1,3,2]-dioxaphosphepin having the formula of Ligand D hereinafter. In a more preferred embodiment, the organomonophosphite ligand is tris(2,4-di-tert-butylphenyl)phosphite.

The hydroformylation process of this invention may be asymmetric or non-asymmetric, the preferred process being non-asymmetric, and is conducted in any continuous or semi-continuous fashion; and may involve any conventional catalyst-containing hydroformylation reaction fluid and/or gas and/or extraction recycle operation, as desired. As used herein, the term "hydroformylation" is contemplated to include all operable asymmetric and non-asymmetric processes that involve converting one or more substituted or unsubstituted olefinic compounds or a reaction mixture comprising one or more substituted or unsubstituted olefinic compounds, in the presence of carbon monoxide, hydrogen, and a hydroformylation catalyst, to a product comprising a mixture of substituted or unsubstituted aldehydes.

The substituted or unsubstituted olefinic compound employable in the hydroformylation process of this invention includes both optically active (prochiral and chiral) and non-optically active (achiral) unsaturated compounds containing from 2 to 40, preferably 3 to 20, carbon atoms and one or more carbon-carbon double bonds (C=C). Such olefinic compounds can be terminally or internally unsaturated and be of straight-chain, branched chain, or cyclic structures. Olefin mixtures, such as obtained from the oligomerization of propene, butene, and isobutene, (such as, so called dimeric, trimeric or tetrameric propylene, as disclosed, for example, in U.S. Pat. Nos. 4,518,809 and 4,528,403, incorporated herein by reference) may also be employed, as well as mixed butenes, for example, raffinate I and raffinate II known to the skilled person. Such olefinic compounds and the corresponding aldehyde products derived therefrom may also contain one or more groups or substituents that do not adversely affect the hydroformylation process of this invention; suitable groups or substituents being described, for example, in U.S. Pat. Nos. 3,527,809, and 4,769,498, incorporated herein by reference.

Most preferably the subject invention is especially useful for the production of non-optically active aldehydes, by hydroformylating achiral alpha-olefins containing from 2 to 30, preferably 3 to 20, carbon atoms, and achiral internal olefins containing from 4 to 20 carbon atoms as well as starting material mixtures of such alpha olefins and internal olefins.

Illustrative alpha and internal olefins include, for example, ethylene, propylene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-methylbutene, 2-pentene, 2-hexene, 3-hexane, 2-heptene, 2-octene, cyclohexene, propylene dimers, propylene trimers, propylene tetramers, butadiene, piperylene, isoprene, 2-ethyl-1-hexene, styrene, 4-methyl styrene, 4-isopropyl styrene, 4-tert-butyl styrene, alpha-methyl styrene, 4-tert-butyl-alpha-methyl styrene, 1,3-diisopropenylbenzene, 3-phenyl-1-propene, 1,4-hexadiene, 1,7-octadiene, 3-cyclohexyl-1-butene, and the like, as well as, 1,3-dienes, butadiene, alkyl alkenoates, for example, methyl pentenoate; alkenyl alkanoates, alkenyl alkyl ethers, alkenols, for example, pentenols; alkenals, for example, pentenals; such species to include allyl alcohol, allyl butyrate, hex-1-en-4-ol, oct-1-en-4-ol, vinyl acetate, allyl acetate, 3-butenyl acetate, vinyl propionate, allyl propionate, methyl methacrylate, vinyl ethyl ether, vinyl methyl ether, allyl ethyl ether, n-propyl-7-octenoate, 3-butenenitrile, 5-hexenamide, eugenol, iso-eugenol, safrole, iso-safrole, anethol, 4-allylanisole, indene, limonene, beta-pinene, dicyclopentadiene, cyclooctadiene, camphene, linalool, oleic acid and esters thereof, such as methyl oleate, and homologous unsaturated fatty acids and unsaturated fatty acid esters. Illustrative of suitable substituted and unsubstituted olefinic starting materials include those olefinic compounds described in Kirk-Othmer, *Encyclopedia of Chemical Technology, Fourth Edition*, 1996, the pertinent portions of which are incorporated herein by reference.

Hydrogen and carbon monoxide are also required for the process of this invention. These gases may be obtained from any available source, including petroleum cracking and refinery operations. Synthesis gas mixtures are preferably employed. The $H_2$:CO molar ratio of gaseous hydrogen to carbon monoxide may range, preferably, from about 1:10 to about 100:1, the more preferred $H_2$:CO molar ratio being from about 1:10 to about 10:1.

In the process of this invention, two different organophosphorus ligands are required, both of which are capable of bonding to a transition metal to form a transition metal-organophosphorus ligand complex catalyst capable of catalyzing the hydroformylation process. One organophosphorus ligand is required to comprise an organopolyphosphite ligand; while the other organophosphorus ligand is required to comprise an organomonophosphite ligand. As the organopolyphosphite ligand, one such ligand or a mixture of such ligands may be used. As the organomonophosphite ligand, one such ligand or a mixture of such ligands may be used. The hydroformylation processing techniques applicable to this invention may correspond to any of the processing techniques known and described in the art. Preferred processes are those involving catalyst liquid recycle hydroformylation processes, as described in U.S. Pat. Nos. 4,668,651; 4,774,361; 5,102,505; 5,110,990; 5,288,918; 5,874,639; and 6,090,987; and extractive hydroformylation processes, as described in U.S. Pat. Nos. 5,932,772; 5,952,530; 6,294,700; 6,303,829; 6,303, 830; 6,307,109; and 6,307,110; the disclosures of which are incorporated herein by reference.

Generally, such catalyzed liquid hydroformylation processes involve production of aldehydes by contacting an olefinic unsaturated compound with carbon monoxide and hydrogen in the presence of a transition metal-organophosphorus ligand complex catalyst in a liquid phase that may also contain an organic solvent for the catalyst and ligand. Free organophosphorus ligand is also present in the liquid phase. In this invention, the generic term "organophosphorus ligand" embraces both types of ligands: organopolyphosphite and organomonophosphite. Both ligands are required; but no inference is made that both ligands are always complexed to the transition metal. Rather, the ligands may be complexed or unbound as catalytic cycling and competition between ligands for transition metal may dictate. By "free organophosphorus ligand" is meant an organophosphorus ligand that is not complexed with (tied to or bound to) the metal, for example, rhodium atom, of the complex catalyst. Generally, the organomonophosphite ligand provides essentially all of the free ligand, because the organomonophosphite is present in excess molar amount relative to the transition metal, whereas the organopolyphosphite is present in a less than stoichiometric amount. Nevertheless, this invention does not exclude the possibility of free organopolyphosphite ligand being present in the reaction fluid. Generally, the hydroformylation process may include a recycle method, wherein a portion of the liquid reaction fluid containing the catalyst and aldehyde product is withdrawn from the hydroformylation reactor (which may include one reaction zone or a plurality of reaction zones, for example, in series), either continuously or intermittently; and the aldehyde product is separated and recovered therefrom by techniques described in the art; and then a metal catalyst-containing residue from the separation is recycled to the reaction zone as disclosed, for example, in U.S. Pat. No. 5,288,918. If a plurality of reaction zones is employed in series, the reactant olefin may be fed to the first reaction zone only; while the catalyst solution, carbon monoxide, and hydrogen may be fed to each of the reaction zones.

As used hereinafter, the term "reaction fluid" or "reaction product fluid" is contemplated to include, but not limited to, a reaction mixture comprising: (a) an organopolyphosphite ligand; (b) an organomonophosphite ligand, wherein at least a portion of the organomonophosphite ligand is free ligand; (c) a transition metal-ligand complex catalyst wherein the ligand is selected from a mixture in the fluid of the organopolyphosphite ligand and the organomonophosphite ligand, (d) two or more aldehyde products formed in the reaction, (e) optionally, unconverted reactants including unreacted olefin, and (f) an organic solubilizing agent for said metal-ligand complex catalyst and said free ligand. It is to be understood that the hydroformylation reaction fluid may contain minor amounts of additional ingredients, such as those that have either been deliberately added or formed in situ during the process. Examples of such additional ingredients include carbon monoxide and hydrogen gases, and in situ formed products, such as saturated hydrocarbons, and/or unreacted isomerized olefins corresponding to the olefin starting materials, and/or high boiling liquid aldehyde condensation byproducts, and/or one or more degradation products of the catalyst and/or organophosphorus ligands, including by-products formed by hydrolysis of the organophosphorus ligands, as well as inert co-solvents or hydrocarbon additives, if employed.

Suitable metals that make up the transition metal-ligand complex catalyst include Group VIII metals selected from rhodium (Rh), cobalt (Co), iridium (Jr), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, and most preferably, rhodium. Other permissible metals include Group VIB metals selected from chromium (Cr), molybdenum (Mo), tungsten (W), and mixtures thereof. Mixtures of metals from Groups VIB and VIII may also be used in this invention.

The term "complex" as used herein means a coordination compound formed by the union of one or more electronically rich molecules or atoms (i.e., ligand) with one or more electronically poor molecules or atoms (i.e., transition metal). For example, the organomonophosphite ligand employable herein possesses one phosphorus (III) donor atom having one unshared pair of electrons, which is capable of forming a coordinate covalent bond with the metal. The organopolyphosphite ligand employable herein possesses two or more phosphorus (III) donor atoms, each having one unshared pair of electrons, each of which is capable of forming a coordinate covalent bond independently or possibly in concert (for example, via chelation) with the transition metal. Carbon monoxide can also be present and complexed with the transition metal. The ultimate composition of the complex catalyst may also contain an additional ligand, for example, hydrogen or an anion satisfying the coordination sites or nuclear charge of the metal. Illustrative additional ligands include, for example, halogen (Cl, Br, I), alkyl, aryl, substituted aryl, acyl, $CF_3$, $C_2F_5$, CN, $(R)_2PO$ and $RP(O)(OH)O$ (wherein each R is the same or different and is a substituted or unsubstituted hydrocarbon radical, for example, alkyl or aryl), acetate, acetylacetonate, $SO_4$, $PF_4$, $PF_6$, $NO_2$, $NO_3$, $CH_3O$, $CH_2=CHCH_2$, $CH_3CH=CHCH_2$, $C_2H_5CN$, $CH_3CN$, $NH_3$, pyridine, $(C_2H_5)_3N$, mono-olefins, diolefins and triolefins, tetrahydrofuran, and the like.

The number of available coordination sites on the transition metal is well known in the art and depends upon the particular transition metal selected. The catalytic species may comprise a complex catalyst mixture in their monomeric, dimeric or higher nuclearity forms, which preferably are characterized by at least one organophosphorus-containing molecule complexed per one molecule of metal, for example, rhodium. For instance, it is considered that the catalytic species of the preferred catalyst employed in the hydroformylation reaction may be complexed with carbon monoxide and hydrogen in addition to either the organopolyphosphite ligand or the organomonophosphite ligand.

The organopolyphosphite ligand broadly comprises a plurality of phosphite groups, each of which contains one trivalent phosphorus atom bonded to three hydrocarbyloxy radicals. Hydrocarbyloxy radicals that link and bridge two phosphite groups are more properly referred to as "divalent hydrocarbyldioxy radicals." These bridging diradicals are not limited to any particular hydrocarbyl species. On the other hand, hydrocarbyloxy radicals that are pendant from a phosphorus atom and not bridging two phosphite groups (i.e., terminal, non-bridging), are each required to consist essentially of an aryloxy radical. The term "aryloxy" as used herein broadly refers to either of two types of aryloxy radicals: (1) a monovalent aryl radical bonded to a single ether linkage, as in —O-aryl, wherein the aryl group comprises a single aromatic ring or multiple aromatic rings that are fused together, directly linked, or indirectly linked (such that different aromatic groups are bound to a common group such as a methylene or ethylene moiety), or (2) a divalent arylene radical bonded to two ether linkages, as in —O-arylene-O— or —O-arylene-arylene-O—, wherein the arylene group comprises a divalent hydrocarbon radical having a single aromatic ring or multiple aromatic rings that are fused together, directly linked, or indirectly linked (such that the different aromatic groups are bound to a common group such as a methylene or ethylene moiety). Preferred aryloxy groups contain one aromatic ring or from 2 to 4 fused or linked aromatic rings, having from about 5 to about 20 carbon atoms, for example, phenoxy, naphthyloxy, or biphenoxy, as well as arylenedioxy radicals, such as, phenylenedioxy, naphthylenedioxy, and biphenylenedioxy. Any of the aforementioned radicals and groups may be unsubstituted or substituted as noted hereinafter.

Preferred organopolyphosphite ligands comprise two, three, or higher numbers of phosphite groups. Mixtures of such ligands may be employed if desired. Achiral organopolyphosphites are preferred. Representative organopolyphosphites include those having the formula:

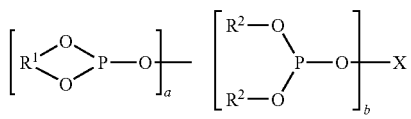
(I)

wherein X represents a substituted or unsubstituted n-valent organic bridging radical containing from 2 to 40 carbon atoms, each $R^1$ is the same or different and represents a divalent arylene radical containing from 6 to 40 carbon atoms, preferably, from 6 to 20 carbon atoms; each $R^2$ is the same or different and represents a substituted or unsubstituted monovalent aryl radical containing from 6 to 24 carbon atoms; a and b can be the same or different and each has a value of 0 to 6, with the proviso that the sum of a+b is 2 to 6 and n equals a+b. Of course it is to be understood that when a has a value of 2 or more, each $R^1$ radical may be the same or different, and when b has a value of 1 or more, each $R^2$ radical may be the same or different.

Representative n-valent (preferably divalent) hydrocarbon bridging radicals represented by X include both acyclic radicals and aromatic radicals, such as alkylene, alkylene-$Q_m$-alkylene, cycloalkylene, arylene, bisarylene, arylene-alkylene, and arylene-$(CH_2)_y$-$Q_m$-$(CH_2)_y$-arylene radicals, wherein each y is the same or different and is a value of 0 or 1. Q represents a divalent bridging group selected from —$C(R^3)_2$—, —O—, —S—, —$NR^4$—, —$Si(R^5)_2$— and —CO—, wherein each $R^3$ is the same or different and represents hydrogen, an alkyl radical having from 1 to 12 carbon atoms, phenyl, tolyl, and anisyl, $R^4$ represents hydrogen or a substituted or unsubstituted monovalent hydrocarbon radical, for example, an alkyl radical having 1 to 4 carbon atoms; each $R^5$ is the same or different and represents hydrogen or an alkyl radical, preferably, a $C_{1-10}$ alkyl radical, and m is a value of 0 or 1. The more preferred acyclic radicals represented by X above are divalent alkylene radicals, while the more preferred aromatic radicals represented by X above are divalent arylene and bisarylene radicals, such as disclosed more fully, for example, in U.S. Pat. Nos. 4,769,498; 4,774,361; 4,885,401; 5,179,055; 5,113,022; 5,202,297; 5,235,113; 5,264,616; 5,364,950; 5,874,640; 5,892,119; 6,090,987; and 6,294,700, the disclosures of which are incorporated herein by reference.

Illustrative preferred organopolyphosphites include bisphosphites such as those of Formulas (II) to (IV) below:

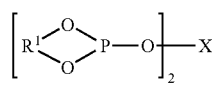
(II)

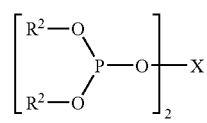
(III)

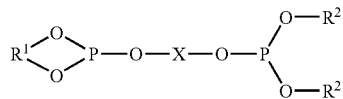
(IV)

wherein $R^1$, $R^2$ and X of Formulas (II) to (IV) are the same as defined above for Formula (I). Preferably X represents a divalent hydrocarbon radical selected from alkylene, arylene, arylene-alkylene-arylene, and bisarylene; $R^1$ represents a divalent hydrocarbon radical selected from arylene, arylene-alkylene-arylene, and bisarylene; and each $R^2$ radical represents a monovalent aryl radical. Organopolyphosphite ligands of such Formulas (II) to (IV) may be found disclosed, for example, in U.S. Pat. Nos. 4,668,651; 4,748,261; 4,769,498; 4,774,361; 4,885,401; 5,113,022; 5,179,055; 5,202,297; 5,235,113; 5,254,741; 5,264,616; 5,312,996; and 5,364,950, the disclosures of which are incorporated herein by reference.

Representative of more preferred classes of organobisphosphites are those of the following Formulas (V) to (VII).

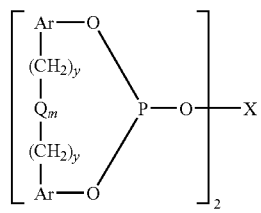
(V)

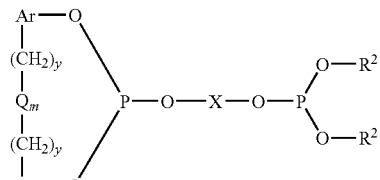
(VI)

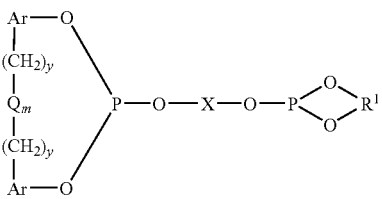
(VII)

wherein Q, $R^1$, $R^2$, X, m, and y are as defined above, and each Ar is the same or different and represents a substituted or unsubstituted divalent aryl radical. Most preferably, X represents a divalent aryl-$(CH_2)_y$-$(Q)_m$-$(CH_2)_y$-aryl radical wherein each y individually has a value of 0 or 1; m has a value of 0 or 1 and Q is —O—, —S— or —$C(R^3)_2$ where each $R^3$ is the same or different and represents hydrogen or a $C_{1-10}$ alkyl radical, preferably, methyl. More preferably, each aryl radical of the above-defined Ar, X, $R^1$ and $R^2$ groups of the above Formulas (V) to (VII) may contain from 6 to 18 carbon atoms and said radicals may be the same or different, while the preferred alkylene radicals of X may contain from 2 to 18 carbon atoms. In addition, preferably the divalent Ar radicals and divalent aryl radicals of X of the above formulas are phenylene radicals in which the bridging group represented by —$(CH_2)_y$-$(Q)_m$-$(CH_2)_y$— is bonded to said phenylene radicals in positions that are ortho to the oxygen atoms of the formulas that connect the phenylene radicals to their phosphorus atom of the formulae. It is also preferred that any substituent radical when present on such phenylene radicals be bonded in the para and/or ortho position of the phenylene radicals in relation to the oxygen atom that bonds the given substituted phenylene radical to its phosphorus atom.

Moreover, if desired any given organopolyphosphite in the above Formulas (I) to (VII) may be an ionic phosphite, that is, may contain one or more ionic moieties selected from the group consisting of: —SO₃M, wherein M represents an inorganic or organic cation, —PO₃M wherein M represents an inorganic or organic cation, —N(R⁶)₃X¹, wherein each R⁶ is the same or different and represents a hydrocarbon radical containing from 1 to 30 carbon atoms, for example, alkyl, aryl, alkaryl, aralkyl, and cycloalkyl radicals, and X¹ represents inorganic or organic anion, —CO₂ M wherein M represents inorganic or organic cation, as described, for example, in U.S. Pat. Nos. 5,059,710; 5,113,022; 5,114,473; and 5,449,653, the disclosures of which are incorporated herein by reference. Thus, if desired, such organopolyphosphite ligands may contain from 1 to 3 such ionic moieties; however, it is preferred that only one such ionic moiety be substituted on any given aryl moiety when the organopolyphosphite ligand contains more than one such ionic moiety. Suitable cationic species of M include, without limitation, hydrogen (that is a proton), the cations of the alkali and alkaline earth metals, for example, lithium, sodium, potassium, cesium, rubidium, calcium, barium, magnesium and strontium, the ammonium cation and quaternary ammonium cations, phosphonium cations, arsonium cations and iminium cations. Suitable anions X¹ include, for example, sulfate, carbonate, phosphate, chloride, acetate, oxalate and the like.

Of course any of the R¹, R², X, Q and Ar radicals of such non-ionic and ionic organopolyphosphites of Formulas (I) to (VII) above may be substituted if desired, with any suitable substituent, optionally containing from 1 to 30 carbon atoms, that does not adversely affect the desired result of the process of this invention. Substituents that may be on said radicals in addition, of course, to corresponding hydrocarbon radicals such as alkyl, aryl, aralkyl, alkaryl and cyclohexyl substituents, may include for example silyl radicals such as —Si(R⁷)₃; amino radicals such as —N(R⁷)₂; phosphine radicals such as -aryl-P(R⁷)₂; acyl radicals such as —C(O)R⁷; acyloxy radicals such as —OC(O)R⁷; amido radicals such as —CON(R⁷)₂ and —N(R⁷)COR⁷; sulfonyl radicals such as —SO₂R⁷; alkoxy radicals such as —OR⁷; sulfinyl radicals such as —SOR⁷; sulfenyl radicals such as —SR⁷; phosphonyl radicals such as —P(O)(R⁷)₂; as well as halogen, nitro, cyano, trifluoromethyl, hydroxy radicals, and the like, wherein preferably each R⁷ radical individually represents the same or different monovalent hydrocarbon radical having from 1 to about 18 carbon atoms (for example, alkyl, aryl, aralkyl, alkaryl and cyclohexyl radicals), with the proviso that in amino substituents such as —N(R⁷)₂ each R⁷ taken together can also represent a divalent bridging group that forms a heterocyclic radical with the nitrogen atom, and in amido substituents such as —C(O)N(R⁷)₂ and —N(R⁷)COR⁷ each R⁷ bonded to N can also be hydrogen. Of course it is to be understood that any of the substituted or unsubstituted hydrocarbon radicals groups that make up a particular given organopolyphosphite may be the same or different.

More specifically illustrative substituents include primary, secondary and tertiary alkyl radicals such as methyl, ethyl, n-propyl, isopropyl, butyl, sec-butyl, t-butyl, neo-pentyl, n-hexyl, amyl, sec-amyl, t-amyl, iso-octyl, decyl, octadecyl, and the like; aryl radicals such as phenyl and naphthyl; aralkyl radicals such as benzyl, phenylethyl, and triphenylmethyl; alkaryl radicals such as tolyl and xylyl; alicyclic radicals such as cyclopentyl, cyclohexyl, 1-methylcyclohexyl, cyclooctyl, and cyclohexylethyl; alkoxy radicals such as methoxy, ethoxy, propoxy, t-butoxy, —OCH₂CH₂OCH₃, —O(CH₂CH₂)₂OCH₃, and —O(CH₂CH₂)₃OCH₃; aryloxy radicals such as phenoxy; as well as silyl radicals such as —Si(CH₃)₃, —Si(OCH₃)₃, and —Si(C₃H₇)₃; amino radicals such as —NH₂, —N(CH₃)₂, —NHCH₃, and —NH(C₂H₅); arylphosphine radicals such as —P(C₆H₅)₂; acyl radicals such as —C(O)CH₃, —C(O)C₂H₅, and —C(O)C₆H₅; carbonyloxy radicals such as —C(O)OCH₃; oxycarbonyl radicals such as —O(CO)C₆H₅; amido radicals such as CONH₂, —CON(CH₃)₂, and —NHC(O)CH₃; sulfonyl radicals such as —S(O)₂C₂H₅; sulfinyl radicals such as —S(O)CH₃; sulfenyl radicals such as —SCH₃, —SC₂H₅, and —SC₆H₅; phosphonyl radicals such as —P(O)(C₆H₅)₂, —P(O)(CH₃)₂, —P(O)(C₂H₅)₂, —P(O)(C₃H₇)₂, —P(O)(C₄H₉)₂, —P(O)(C₆H₁₃)₂, —P(O)CH₃(C₆H₅), and —P(O)(H)(C₆H₅).

Specific illustrative examples of such organobisphosphite ligands include the following:

6,6'-[[4,4'-bis(1,1-dimethylethyl)-[1,1'-binaphthyl]-2,2'-diyl]bis(oxy)]bis-dibenzo[d,f][1,3,2]-dioxaphosphepin having the formula:

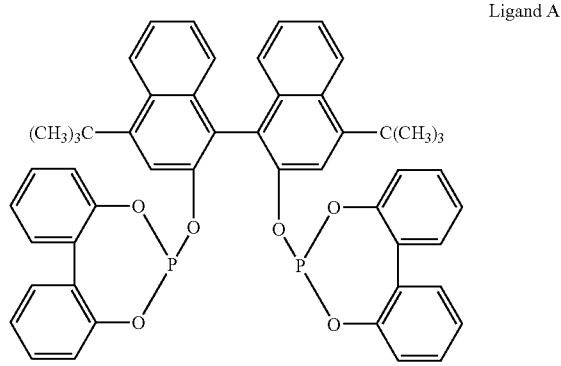

Ligand A 6,6'-[[3,3'-bis(1,1-dimethylethyl)-5,5'-dimethoxy-[1,1'-biphenyl]-2,2'-diyl]bis(oxy)]bis-dibenzo[d,f][1,3,2]dioxaphosphepin having the formula:

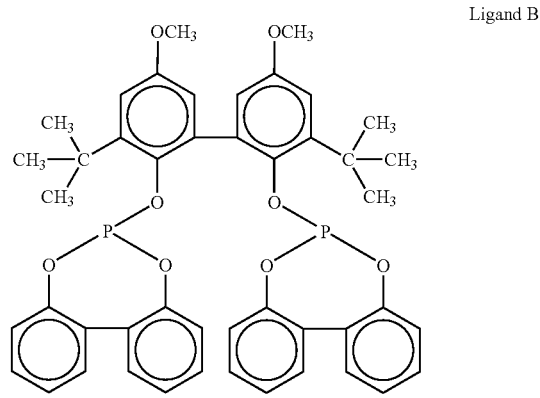

Ligand B 6,6'-[[3,3',5,5'-tetrakis(1,1-dimethylpropyl)-[1,1'-biphenyl]-2,2'-diyl]bis(oxy)]bis-dibenzo[d,f][1,3,2]dioxaphosphepin having the formula:

6,6'-[[3,3',5,5'-tetrakis(1,1-dimethylethyl)-[1,1'-biphenyl]-2,2'-diyl]bis(oxy)]bis-dibenzo[d,f][1,3,2]-dioxaphosphepin having the formula:

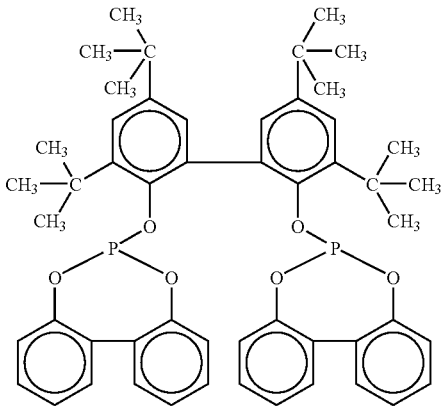

Ligand D

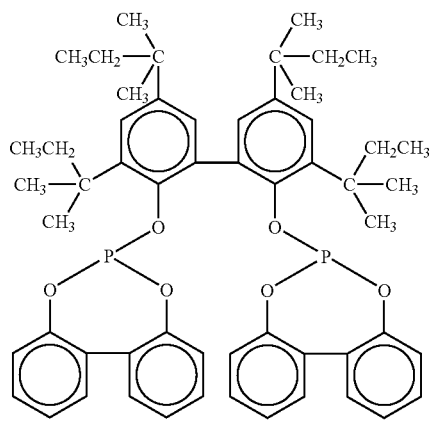

Ligand C (a more preferred species)

(2R,4R)-di[2,2'-(3,3',5,5'-tetrakis-tert-amyl-1,1'-biphenyl)]-2,4-pentyldiphosphite having the formula:

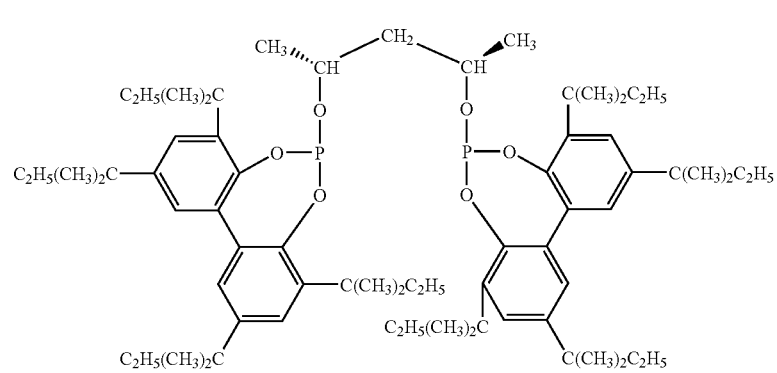

Ligand E (2R,4R)-di[2,2'-(3,3',5,5'-tetrakis-tert-butyl-1,1'-biphenyl)]-2,4-pentyldiphosphite having the formula:

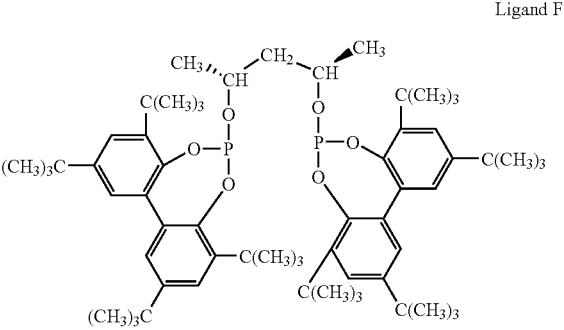

Ligand F (2R,4R)-di[2,2'-(3,3'-di-amyl-5,5'-dimethoxy-1,1'-biphenyl)]-2,4-pentyldiphosphite having the formula:

Ligand G

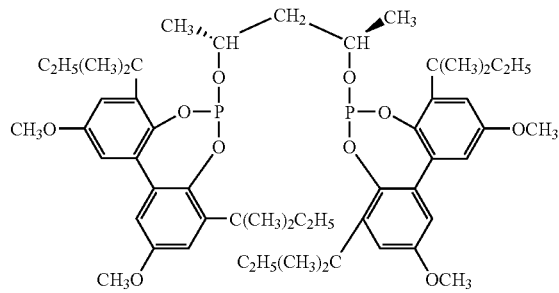

(2R,4R)-di[2,2'-(3,3'-di-tert-butyl-5,5'-dimethyl-1,1'-biphenyl)]-2,4-pentyldiphosphite having the formula:

Ligand H

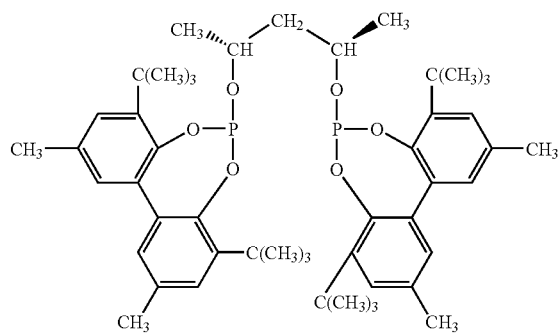

(2R,4R)-di[2,2'-(3,3'-di-tert-butyl-5,5'-diethoxy-1,1'-biphenyl)]-2,4-pentyldiphosphite having the formula:

Ligand I

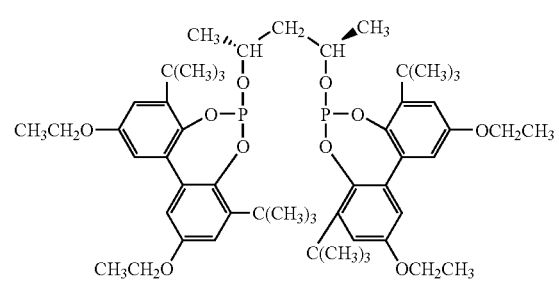

(2R,4R)-di[2,2'-(3,3'-di-tert-butyl-5,5'-diethyl-1,1'-biphenyl)]-2,4-pentyldiphosphite having the formula:

Ligand J

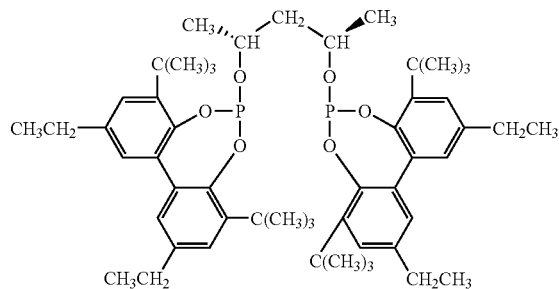

(2R,4R)-di[2,2'-(3,3'-di-tert-butyl-5,5'-dimethoxy-1,1'-biphenyl)]-2,4-pentyldiphosphite having the formula:

Ligand K

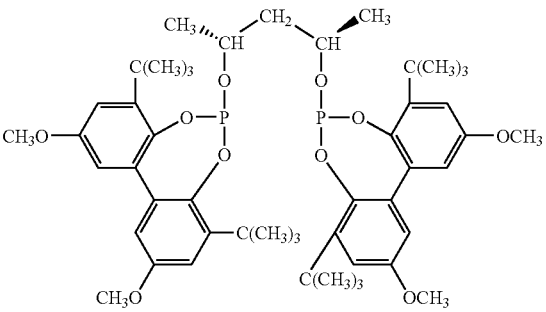

6-[[2'-[(4,6-bis(1,1-dimethylethyl)-1,3,2-benzodioxaphosphol-2-yl)oxy]-3,3'-bis(1,1-dimethylethyl)-5,5'-dimethoxy[1,1'-biphenyl]-2-yl]oxy]-4,8-bis(1,1-dimethylethyl)-2,10-dimethoxydibenzo[d,f][1,3,2]dioxaphosphepin having the formula:

Ligand L

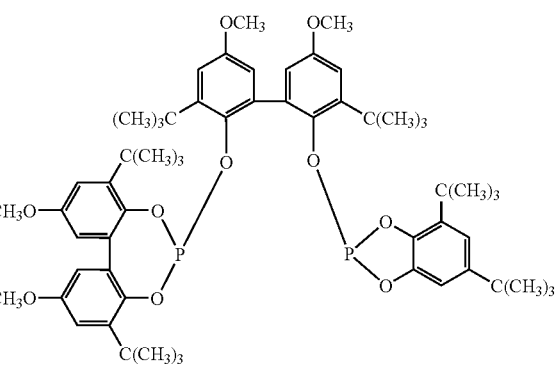

6-[[2'-[1,3,2-benzodioxaphosphol-2-yl)oxy]-3,3'-bis(1,1-dimethylethyl)-5,5'-dimethoxy[1,1'-biphenyl]-2-yl]oxy]-4,8-bis(1,1-dimethylethyl)-2,10-dimethoxydibenzo[d,f][1,3,2]dioxaphosphepin having the formula:

Ligand M

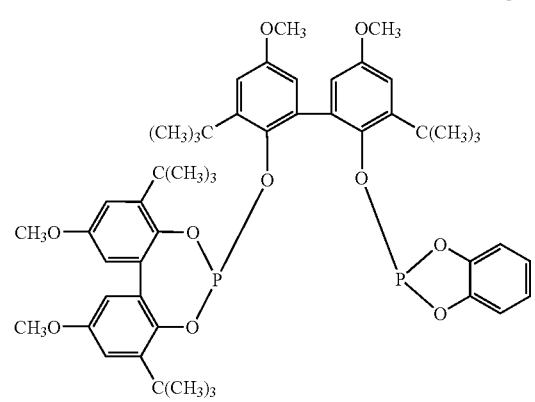

2'-[[4,8-bis(1,1-dimethylethyl)-2,10-dimethoxydibenzo[d,f][1,3,2]-dioxaphosphepin-6-yl]oxy]-3,3'-bis(1,1-dimethylethyl)-5,5'-dimethoxy[1,1'-biphenyl]-2-yl bis(4-hexylphenyl)ester of phosphorous acid having the formula:

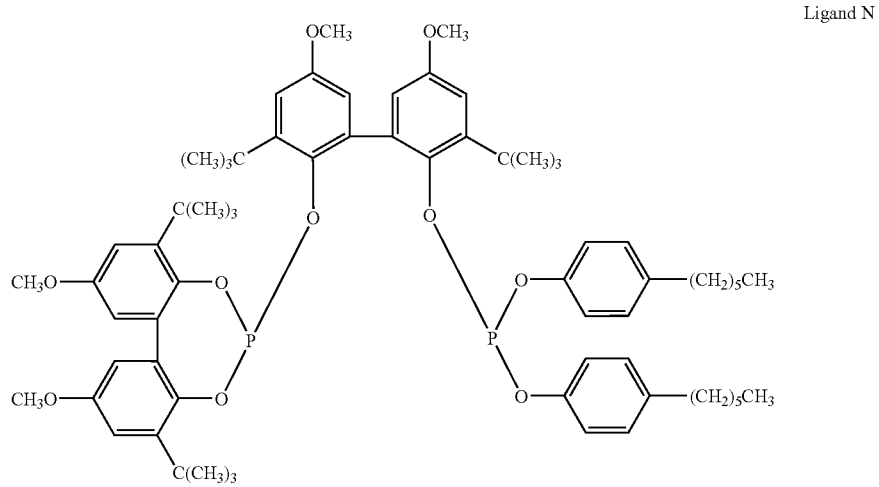

Ligand N

2-[[2-[[4,8,-bis(1,1-dimethylethyl), 2,10-dimethoxy-dibenzo-[d,f][1,3,2]dioxophosphepin-6-yl]oxy]-3-(1,1-dimethylethyl)-5-methoxyphenyl]methyl]-4-methoxy, 6-(1,1-dimethylethyl)phenyl diphenyl ester of phosphorous acid having the formula:

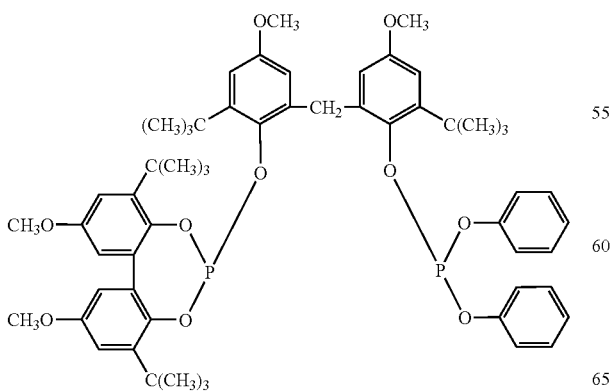

Ligand O 3-methoxy-1,3-cyclohexamethylene tetrakis[3,6-bis(1,1-dimethylethyl)-2-naphthalenyl]ester of phosphorous acid having the formula:

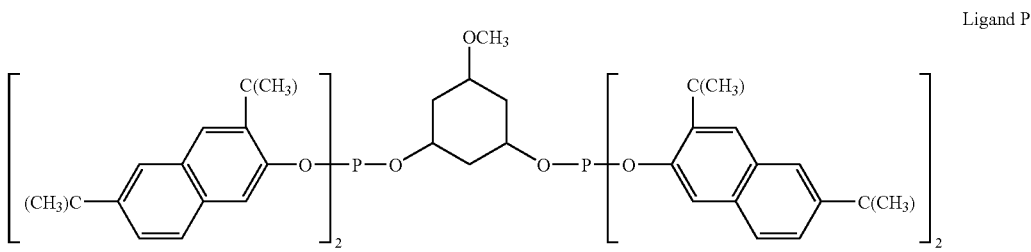

Ligand P 2,5-bis(1,1-dimethylethyl)-1,4-phenylene tetrakis[2,4-bis(1,1-dimethylethyl)phenyl]ester of phosphorous acid having the formula:

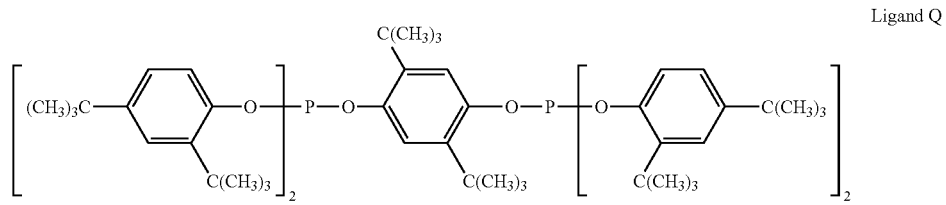

Ligand Q methylenedi-2,1-phenylene tetrakis[2,4-bis(1,1-dimethylethyl)phenyl]ester of phosphorous acid having the formula:

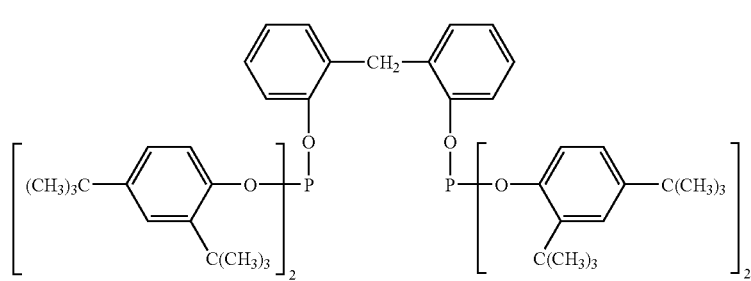

Ligand R

[1,1'-biphenyl]-2,2'-diyl tetrakis[2-(1,1-dimethylethyl)-4-methoxyphenyl]ester of phosphorous acid having the formula:

Ligand S

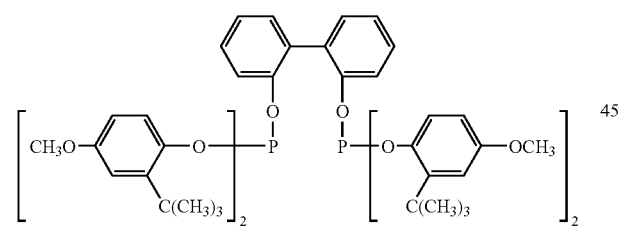

The organomonophosphite employable in the process of this invention comprises any organic compound comprising one phosphite group. A mixture of organomonophosphite ligands may also be employed. Representative organomonophosphites include those having the formula:

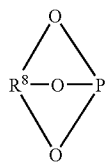

(VIII)

wherein $R^8$ represents a substituted or unsubstituted trivalent hydrocarbon radical containing from 4 to 40 carbon atoms or greater, such as trivalent acyclic and trivalent cyclic radicals, e.g., trivalent alkylene radicals such as those derived from 1,2,2-trimethylolpropane, or trivalent cycloalkylene radicals, such as those derived from 1,3,5-trihydroxycyclohexane.

Such organomonophosphites may be found described in greater detail, for example, in U.S. Pat. No. 4,567,306, the disclosure of which is incorporated herein by reference.

Representative diorganophosphites may include those having the formula:

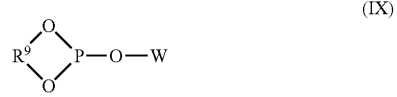

(IX)

wherein $R^9$ represents a substituted or unsubstituted divalent hydrocarbon radical containing from 4 to 40 carbon atoms or greater and W represents a substituted or unsubstituted monovalent hydrocarbon radical containing from 1 to 18 carbon atoms.

Representative substituted and unsubstituted monovalent hydrocarbon radicals represented by W in the above formula include alkyl and aryl radicals, while representative substituted and unsubstituted divalent hydrocarbon radicals represented by $R^9$ include divalent acyclic radicals and divalent aromatic radicals. Illustrative divalent acyclic radicals include, for example, alkylene, alkylene-oxy-alkylene, alkylene-$NX^2$-alkylene, wherein $X^2$ is hydrogen or a substituted or unsubstituted hydrocarbon radical, alkylene-S-alkylene, and cycloalkylene radicals. The more preferred divalent acyclic radicals are the divalent alkylene radicals, such as disclosed more fully, for example, in U.S. Pat. Nos. 3,415,906 and 4,567,302, the disclosures of which are incorporated herein by reference. Illustrative divalent aromatic radicals include, for example, arylene bisarylene, arylene-alkylene, arylene-alkylene-arylene, arylene-oxy-arylene, arylene-NX²-arylene, wherein X² is as defined above, arylene-S-arylene, and arylene-S-alkylene. More preferably, $R^9$ is a divalent aromatic radical, such as disclosed more fully, for example, in U.S. Pat. Nos. 4,599,206 and 4,717,775, the disclosures of which are incorporated herein by reference.

Representative of a more preferred class of diorganomonophosphites are those of the formula:

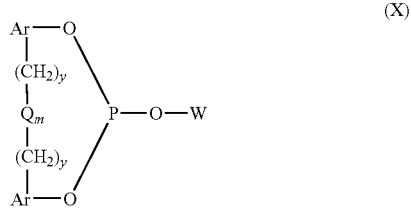

(X)

wherein W is as defined above, each Ar is the same or different and represents a substituted or unsubstituted divalent aryl radical, each y is the same or different and is a value of 0 or 1, Q represents a divalent bridging group selected from —C($R^{10}$)₂—, —O—, —S—, —N$R^{11}$—, —Si($R^{12}$)₂— and —CO, wherein each $R^{10}$ is the same or different and represents hydrogen, alkyl radicals having from 1 to 12 carbon atoms, phenyl, tolyl, and anisyl, $R^{11}$ represents hydrogen or an alkyl radical of from 1 to 10 carbon atoms, preferably, methyl, each $R^{12}$ is the same or different and represents hydrogen or an alkyl radical having from 1 to about 10 carbon atoms, preferably, methyl, and m is a value of 0 or 1. Such diorganomonophosphites are described in greater detail, for example, in U.S. Pat. Nos. 4,599,206, 4,717,775, and 4,835,299, the disclosures of which are incorporated herein by reference.

Representative triorganomonophosphites may include those having the formula:

(XI)

wherein each $R^{13}$ is the same or different and is a substituted or unsubstituted monovalent hydrocarbon radical, for example, an alkyl, cycloalkyl, aryl, alkaryl, or aralkyl radical, which may contain from 1 to 24 carbon atoms. Illustrative triorganomonophosphites include, for example, trialkylphosphites, dialkylarylphosphites, alkyldiarylphosphites, and triarylphosphites, such as, triphenylphosphite, tris(2,6-triisopropyl)phosphite, tris(2,6-di-tert-butyl-4-methoxyphenyl)phosphite, as well as the more preferred tris(2,4-di-tert-butylphenyl)phosphite. The monovalent hydrocarbon radical moieties themselves may be functionalized with the proviso that said functional groups do not significantly interact with the transition metal or otherwise inhibit hydroformylation. Representative functional groups include alkyl or aryl radicals, ethers, nitriles, amides, esters, —N($R^{11}$)₂, —Si($R^{12}$)₃, phosphates, and the like, wherein $R^{11}$ and $R^{12}$ are defined hereinbefore. Such triorganomonophosphites are described in more detail in U.S. Pat. Nos. 3,527,809 and 5,277,532, the disclosures of which are incorporated herein by reference.

As a further option, any organomonophosphite-monophosphate ligand or organomonophosphite-polyphosphate ligand may be employed as the organomonophosphite ligand in this invention. For example, any of the organopolyphosphite ligands, including preferred organobisphosphite ligands, which are described hereinbefore may be subjected to oxidation such that all but one of the phosphorus (III) atoms is converted into phosphorus (V) atoms. The resulting oxidized ligand can comprise an organomonophosphite-polyphosphate or, preferably, an organomonophosphite-monophosphate, which suitably is employed in a 2/1 molar excess relative to transition metal so as to provide for the organomonophosphite ligand component of this invention.

The concentration of metal-ligand complex(es) present in the reaction fluid of the hydroformylation process of this invention need only be that minimum amount necessary to provide a metal concentration necessary to catalyze the desired hydroformylation process. Generally, in the hydroformylation of propylene, the metal concentration, preferably, rhodium concentration, is greater than about 1 part per million (ppm), and preferably, greater than about 20 ppm, based on the weight of the hydroformylation reaction fluid. Generally, in the hydroformylation of propylene, the metal concentration is less than about 120 parts per million (ppm), preferably, less than about 95 ppm, based on the weight of the hydroformylation reaction fluid. For C4+ olefins, such as butene and those of higher molecular weights, suitable concentrations of metal may be higher, because higher olefins exhibit reduced activity as compared with propylene. Even so, the concentration ranges are advantageously lower than the corresponding ranges employed in organophosphine-based hydroformylation plants, wherein upwards of 200 to 400 ppm transition metal are employed for propylene hydroformylation.

The organomonophosphite ligand employable in the process of this invention, including free and complexed forms, is provided to the process in a super-stoichiometric quantity, which means that the molar ratio of organomonophosphite ligand to transition metal present in the hydroformylation reaction fluid is greater than 2/1 (i.e., greater than 2 mole P(III) per mole transition metal). Preferably, the quantity of organomonophosphite ligand, including free and complexed forms, is greater than 2 moles, preferably greater than about 3 moles, and more preferably, greater than about 4 moles per mole transition metal present in the reaction fluid. Preferably, the quantity of organomonophosphite ligand, including free and complexed forms, is less than about 100 moles, more preferably, less than about 50 moles, and most preferably, less than about 20 moles organomonophosphite ligand per mole of transition metal present in the reaction fluid.

The process of this invention operates at a sub-stoichiometric quantity of organopolyphosphite ligand relative to transition metal present in the hydroformylation reaction fluid, which means that the molar ratio of organopolyphosphite ligand, including both free and complexed forms, to transition metal in the reaction fluid is less than 1.0/1. The quantity of organopolyphosphite ligand is greater than 0, but preferably, greater than about 0.01 mole organopolyphosphite ligand per mole transition metal present in the reaction fluid.

In this invention, continuous flexibility of the N/I isomer ratio is achieved by varying the molar ratio of organopolyphosphite ligand to transition metal within the sub-stoichiometric range (<1.0/1), while maintaining the molar ratio of organomonophosphite ligand to transition metal within the super-stoichiometric range (>2/1). Without being limited to a specific mechanism, it is thought that the organopolyphosphite binds more strongly to the transition metal due to a chelation effect; thus most, if not all, of the organopolyphosphite ligand is bound to transition metal and forms an active catalyst. The remaining Rh is complexed by the excess organomonophosphite and also forms its own active catalyst. Thus, the resulting mixture produces the weighted average performance of the two complexes and the N/I ratio is controlled by deliberately controlling the ratio of the two catalysts. More specifically, at the super-stoichiometric ratio of organomonophosphite ligand to transition metal, the concentration of organopolyphosphite ligand can be adjusted to maintain a selected sub-stoichiometric molar ratio of said polyphosphite ligand to transition metal, thereby maintaining a desired or "target" N/I isomer ratio of the product aldehydes. Alternatively, the concentration of organopolyphosphite ligand can be varied upwards or downwards to elect a new molar ratio of said polyphosphite ligand to transition metal, resulting in variation of the N/I product isomer ratio upwards or downwards. Generally, increasing the organopolyphosphite ligand concentration relative to that of transition metal increases the N/I isomer ratio, and decreasing the organopolyphosphite ligand concentration relative to that of transition metal decreases the N/I isomer ratio; although this invention is not limited to such a specific trend.

The concentrations of transition metal, organopolyphosphite ligand, and organomonophosphite ligand in the hydroformylation reaction fluid can be readily determined by well known analytical methods. From these concentration analyses, the required molar ratios can be readily calculated and tracked. The transition metal, preferably rhodium, is best determined by atomic absorption or inductively coupled plasma (ICP) techniques. The ligands are best quantized by $^{31}$P nuclear magnetic resonance spectroscopy (NMR) or by high pressure liquid phase chromatography (HPLC) of aliquots of the reaction fluid. On-line HPLC can also be used to monitor the concentrations of the ligands and the transition metal-ligand complexes. The different ligands should be characterized separately (e.g., without the presence of transition metal in the reaction fluid) in a quantitative manner to establish chemical shifts and/or retention times using appropriate internal standards as needed. The transition metal-organopolyphosphite ligand and transition metal-organomonophosphite ligand complexes can be observed via any of the above-identified analytical methods to enable quantification of the complexed ligand(s).

Equation 1 hereinafter can be used to calculate the molar ratio of organopolyphosphite ligand to transition metal ($X_{OPP}$) in the reaction fluid.

$$X_{OPP} = \frac{\Sigma[\text{free organopolyphosphite ligand} + \text{M-organopolyphosphite ligand}]}{\Sigma[\text{M-organopolyphosphite ligand} + \text{M-organomonophosphite ligand}]} \quad \text{(Equation 1)}$$

Wherein M represents the transition metal; "free organopolyphosphite ligand" represents the moles of free or uncomplexed organopolyphosphite ligand; "M-organopolyphosphite ligand" represents the moles of metal-organopolyphosphite ligand complex; and "M-organomonophosphite ligand" represents the moles of metal-organomonophosphite ligand.

Equation 2 can be used to calculate the molar ratio of organomonophosphite ligand to transition metal ($X_{OMP}$) in the reaction fluid.

$$X_{OMP} = \frac{\Sigma[\text{free organomonophosphite ligand} + \text{M-organomonophosphite ligand}]}{\Sigma[\text{M-organopolyphosphite ligand} + \text{M-organomonophosphite ligand}]} \quad \text{(Equation 2)}$$

Wherein "free organomonophosphite ligand" represents the moles of free or uncomplexed organomonophosphite ligand; and wherein "M" and "M-organopolyphosphite ligand," and "M-organomonophosphite ligand" are identified hereinabove.

The concentration of organopolyphosphite ligand in the hydroformylation reaction fluid can be increased in any suitable manner, for example, by adding a quantity of organopolyphosphite ligand in one batch or in incremental additions to the hydroformylation reactor, or by continuously or intermittently adding a quantity of organopolyphosphite ligand to a liquid feed to the reactor comprising solubilizing agent (solvent), catalyst, organomonophosphite ligand, and optionally liquid olefinic compound. Alternatively, organopolyphosphite ligand can be added into a recycle stream (or a unit that produces a recycle stream) at any point downstream of the hydroformylation reactor for cycling back to said reactor. For example, organopolyphosphite ligand can be added to an extractor that processes the hydroformylation product fluid to recover a recycle stream containing the organomonophosphite, the original and additional quantities of organopolyphosphite, and a solubilizing agent, which are cycled back to the hydroformylation reactor. Likewise, the concentration of organopolyphosphite ligand in the hydroformylation reaction fluid can be decreased in any suitable manner; for example, the concentration of organopolyphosphite ligand can be decreased over time through hydrolytic attrition resulting from reaction of the ligand with quantities of water present in the reaction fluid. Alternatively, if it is desirable to lower the molar ratio of organopolyphosphite ligand to transition metal (and hence the N/I isomer ratio) more quickly, a suitable quantity of additional water can be deliberately added to the hydroformylation reaction fluid to accelerate organopolyphosphite ligand hydrolysis. Alternatively, a suitable quantity of oxidant, such as oxygen, air, hydrogen peroxide, organic hydroperoxides, more specifically, alkyl hydroperoxides, such as tertiary-butyl hydroperoxide, or aryl hydroperoxides, such as ethylbenzene hydroperoxide or cumene hydroperoxide, can be deliberately added to the hydroformylation reaction fluid to accelerate destructive oxidation of the organopolyphosphite ligand. At any time during the continuous hydroformylation process, additional organopolyphosphite and/or organomonophosphite ligand(s) can be supplied to the reaction fluid to make-up for such ligand lost through degradation. Other methods may be employed to lower the concentration of organopolyphosphite ligand relative to transition metal. For example, downstream extraction or vaporization of the hydroformylation product stream may be conducted under process conditions (e.g., pH or elevated temperature) selected to degrade a portion of the organopolyphosphite ligand so as to reduce its concentration in a recycle stream returning to the hydroformylation reactor. The skilled process engineer may envision other means and methods of raising or lowering the organopolyphosphite concentration relative to transition metal.

In this invention, variation in the molar ratio of organopolyphosphite ligand to transition metal controls the N/I isomer ratio in the aldehyde product. In practice, the observed N/I isomer ratio of the aldehyde product indicates whether to add organopolyphosphite ligand (typically to increase the N/I ratio) or to add water or oxidant (typically to lower the N/I ratio). The degree to which one chooses to raise or lower the isomer ratio is governed by the selected target N/I isomer ratio (e.g., as determined by market demands). For a small degree of deviation (<+/−1) from the target N/I ratio, a preferred practice is to add unit portions of the organopolyphosphite ligand or water or oxidant to the reactor intermittently until the target N/I ratio is reached. The "unit portion" consists of a molar charge of organopolyphosphite ligand or water or oxidant taken as about 5 to about 10 mole percent of the initial moles of organopolyphosphite charged to the reactor. For a large degree of deviation (>+/−1) from the target N/I ratio, several unit portions can be combined into larger portions that are added to the reactor. In continuous operation, a continuous or intermittent addition of the unit portion of organopolyphosphite ligand or water or oxidant can be made directly into the reactant feed to the reactor or via a separate feed line. In continuous operations, one may choose to time the additions of the organopolyphosphite ligand based on prior experience with the rate of decay of said ligand to achieve stable organopolyphosphite ligand concentration with a resulting desired and stable N/I isomer ratio. The N/I isomer ratio is readily determined by GC analysis of the product stream from the reactor either from the vapor space (e.g., a vent stream) or liquid sample of the product fluid taken directly from the reactor or from a downstream product-catalyst separation stage (e.g., vaporizer).

In this invention, control over the N/I isomer ratio is usually smooth and continuous rather than discontinuous or abrupt, such as, a "step-ladder" increase or decrease. For the purposes of this invention, a "discontinuity" may be construed to mean a greater than +/−1 change in the N/I isomer ratio per unit addition of organopolyphosphite ligand or water or oxidant.

In general, the hydroformylation process of this invention can be conducted at any operable reaction temperature. Preferably, the reaction temperature is greater than about −25° C., more preferably, greater than about 50° C. Preferably, the reaction temperature is less than about 200° C., preferably, less than about 120° C.

The hydroformylation process of this invention is required to be conducted in a reaction regime wherein the hydroformylation reaction rate is of a negative or inverse order with respect to carbon monoxide partial pressure. As used herein, the term "hydroformylation reaction rate" is defined as gram-moles of carbon monoxide consumed or aldehyde produced per liter of reaction fluid volume per hour (g-mol/l/h), measured at a specified set of operating conditions. (Since there is a 1:1 correlation between CO consumed and aldehyde produced, the rate can be expressed either way as may be convenient.) With reference to FIG. 1 (region 2), a hydroformylation reaction rate that is "negative or inverse order" with respect to carbon monoxide partial pressure refers to CO partial pressures wherein the hydroformylation reaction rate increases as carbon monoxide partial pressure decreases, and wherein the hydroformylation reaction rate decreases as carbon monoxide partial pressure increases. In contrast, with reference to FIG. 1 (region 1), a hydroformylation reaction rate that is "positive order" with respect to carbon monoxide partial pressure refers to CO partial pressures wherein the hydroformylation reaction rate increases as carbon monoxide partial pressure increases, and wherein the hydroformylation reaction rate decreases as carbon monoxide partial pressure decreases.

In this invention, an operable range of carbon monoxide partial pressures in the negative order regime should be pre-determined from a plot of hydroformylation reaction rate as a function of CO partial pressure as measured on a "control" hydroformylation process. The control process establishes the CO partial pressures in negative order regime for the organopolyphosphite ligand, which is the ligand that needs to be stabilized against unacceptable hydrolysis. The control process, therefore, employs solely the organopolyphosphite ligand at a molar ratio to transition metal in excess of 1/1 and in the absence of the organomonophosphite ligand. (In the control, the molar ratio of organopolyphosphite ligand to transition metal is greater than 1/1, because otherwise, inactive and uncomplexed transition metal would precipitate from the reaction solution. Moreover, excess organopolyphosphite ligand in the control reaction has essentially no effect upon the measured rate of reaction and N/I isomer ratio.) In the control (or pre-determination step), the process conditions employed are otherwise identical to those intended for the subject invention. The word "identical" means that the process conditions for the control experiment are identically matched to the selected embodiment of the subject invention, including specific olefinic reactant, composition of syngas feed, $H_2$:CO molar ratio, solubilizing agent, transition metal, concentrations of olefin reactant and transition metal, flow rates, temperature, and any other operating conditions, with exception that no organomonophosphite ligand is used and the concentration of organopolyphosphite ligand is set at greater than 1/1 and, preferably, up to about 5/1.

Reference is made to WO 2006/020287, incorporated herein by reference, which enables and illustrates construction of the hydroformylation rate curve as a function of carbon monoxide partial pressure. Selection of a carbon monoxide partial pressure that resides in the negative order region of the rate curve can be most conveniently determined in a continuous reactor that allows for steady-state operation during data collection. For the purposes of this invention, "steady state operation" is defined for a continuous process wherein the hydroformylation reaction rate, the rate of olefin and syngas consumption, olefin conversion, reactor pressure, and reactor temperature are substantially constant, within +/−5 percent over a running average of measurements taken at least about every hour for at least about 3 hours. The hydroformylation reactor is preferably equipped with an impeller, impeller shaft, olefin feed line and flow control, syngas feed line and flow control, a vent line and vent flow control, a total pressure sensor for sensing pressure within the reactor, an exit line for removing product fluid from the reactor, and an entry line for feeding recovered catalyst back to the reactor. The syngas feed line typically terminates in the reactor with a sparger. Optionally, the reactor may include one or more baffles that separate the inner chamber of the reactor into a plurality of reaction zones. Typically, each baffle is attached to the inner wall of the reactor and extends into the reactor perpendicular to the impeller shaft; and each baffle contains an opening or hole of sufficient size for passage of the impeller shaft as well as passage of reaction fluid and gases. Typically, each chamber or zone in the reactor formed by such baffles contains an impeller as well as a gas sparger for circulating and mixing the reaction fluid in that chamber or zone.

At the start, a variety of process parameters are selected including a specific unsaturated olefinic compound or mixture of olefinic compounds, a transition metal-organopolyphosphite ligand complex catalyst, a concentration of transition metal, a total concentration of free and complexed organopolyphosphite ligand, a solvent, a reaction temperature, an olefin feed rate, and a syngas $H_2$:CO mole ratio. An initial syngas feed rate is selected that is stoichiometrically less than the olefin feed rate, preferably, less than ½ the stoichiometric feed rate relative to the olefin feed rate. A vent flow rate from the reactor is also selected. Typically, all variables are fixed with the exception of syngas feed flow rate and total pressure.

After the above parameters are established, a syngas feed flow is started. After the reaction reaches a steady-state operation, the total pressure is detected and recorded. In the initial phase of this evaluation, excess olefin feed is present, and the reaction system is rate limited by the sub-stoichiometric syngas feed. Then, the syngas feed flow is increased. As the syngas feed flow is increased at fixed olefin feed rate (and because typically initially the reaction is positive order in carbon monoxide), the total system pressure steadily declines as more carbon monoxide and hydrogen are available to satisfy the stoichiometry of the hydroformylation reaction. The total pressure continues to decline, until the carbon monoxide partial pressure is sufficiently high to cross into the negative order region of the rate curve. When that point is reached, the total pressure climbs suddenly and dramatically since each incremental addition of carbon monoxide partial pressure slows or quenches the hydroformylation rate. Carbon monoxide partial pressures in the negative order region of the rate curve are selected from partial pressures greater than the cross-over partial pressure. Total pressures are selected from the range of total pressures measured in the negative order region of the curve. The carbon monoxide partial pressure is determined by measuring the gas composition (typically by GC analysis of the vapor space) to determine mole percent composition of the vapor space under the reaction conditions and using Dalton's law. A plot of reaction rate, taken as g-mole aldehyde product per liter reaction volume per hour can be constructed as a function of CO partial pressure, as in FIG. 1.

In view of the above, the minimum total pressure suitable for the hydroformylation process of this invention is defined by the amount of carbon monoxide necessary to enter the negative or inverse order region of the rate curve, which depends upon the specific composition of the hydroformylation reaction fluid employed. Generally, the total gas pressure comprising carbon monoxide, hydrogen, and olefinic reactant(s) may range from about 1 psia (6.8 kPa) to about 10,000 psia (69,000 MPa). In general, however, it is preferred that the process be operated at a total gas pressure comprising carbon monoxide, hydrogen, and olefin reactant(s) of greater than about 25 psia (172 kPa) and less than about 2,000 psia (6,895 kPa) and more preferably less than about 500 psia (3500 kPa). More specifically the carbon monoxide partial pressure of the hydroformylation process of this invention may vary from about 10 psia (68 kPa) to about 1,000 psia (6,900 kPa), and more preferably from about 10 psia (68 kPa) to about 800 psia (5,500 kPa), and even more preferably, from about 15 psia (103.4 kPa) to about 100 psia (689 kPa); while the hydrogen partial pressure ranges preferably from about 5 psia (34.5 kPa) to about 500 psia (3,500 kPa), and more preferably from about 10 psia (69 kPa) to about 300 psia (2,100 kPa).

The syngas feed flow rate may be any operable flow rate sufficient to obtain the desired hydroformylation process. Typically, the syngas feed flow rate can vary widely depending upon the specific form of catalyst, olefin feed flow rate, and other operating conditions. Suitable syngas feed flow rates and vent flow rates are described in the following reference: "Process Economics Program Report 21D: Oxo Alcohols 21d," SRI Consulting, Menlo Park, Calif., Published December 1999, incorporated herein by reference.

As noted, the aforementioned control experiment provides important information on the rate of hydroformylation as a function of CO partial pressure (e.g., FIG. 1), the range of CO partial pressures in the negative order region of the hydroformylation rate curve, and the N/I isomer ratios achievable when using solely the organopolyphosphite ligand Likewise, an analogous control experiment should be conducted in the presence solely of the organomonophosphite ligand and in the absence of the organopolyphosphite ligand, to obtain information on the rate of hydroformylation and the N/I isomer ratios achievable with the organomonophosphite ligand. With the above control data in hand, the organopolyphosphite ligand to transition metal molar ratio required to achieve the target N/I isomer ratio in the mixed ligand system of this invention can be estimated by Equation 3 as follows:

$$\text{Linear:branched\_ratio} = \frac{\left[Rate_{(mono)} * (1 - X_{OPP}) * \frac{N_{mono}}{[N_{mono} + 1]}\right] + \left[Rate_{(poly)} * X_{OPP} * \frac{N_{poly}}{[N_{poly} + 1]}\right]}{\left[Rate_{(mono)} * (1 - X_{OPP}) * \frac{1}{[N_{mono} + 1]}\right] + \left[Rate_{(poly)} * X_{OPP} * \frac{1}{[N_{poly} + 1]}\right]} \quad \text{(Equation 3)}$$

wherein:

$Rate_{(mono)}$=hydroformylation rate of the M-organomonophosphite catalyst.

$Rate_{(poly)}$=hydroformylation rate of the M-organopolyphosphite catalyst.

$N_{mono}$=moles linear isomer per mole branched isomer produced with the M-organomonophosphite catalyst.

$N_{poly}$=moles linear isomer per mole branched isomer produced with the M-organopolyphosphite catalyst.

$X_{OPP}$=mole fraction of "M" bound to the organopolyphosphite, wherein in all of the above, M is the transition metal. (We note that the linear to branched molar ratios normally represented by "N/I" are abbreviated in Equation 3 to "N" to simplify the notation in the equation.) $Rate_{(mono)}$, $Rate_{(poly)}$, $N_{mono}$, mono, and $N_{poly}$ are determined separately in the control experiments described above. The values of $X_{OPP}$ can be measured analytically (e.g., $^{31}P$ NMR, HPLC, AA), but typically essentially equals the organopolyphosphite/transition metal mole ratio. For any target N/I isomer ratio in the mixed ligand system, the value of $X_{OPP}$ can be calculated using Equation 3 to establish the desired amount of organopolyphosphite in moles, relative to moles transition metal, to be charged to the reactor. For example, if two ligands have the same hydroformylation rate and a Rh-organomonophosphite catalyst gives an N/I isomer ratio of 1:1, while a Rh-organopolyphosphite catalyst gives an isomer ratio of 20:1 under the same reaction conditions, then to obtain a target isomer ratio of 10:1, the organopolyphosphite:Rh molar ratio ($X_{OPP}$) is estimated to be 0.90. In fact, a plot of N/I versus $X_{OPP}$ can be constructed based on the above example, as illustrated in FIG. 2 (and Table 1 hereinafter), and used to estimate the molar ratio of organopolyphosphite ligand to transition metal for the above example over a range of $X_{OPP}$ from 0.3 to 1.0.

TABLE 1

Figure 2:
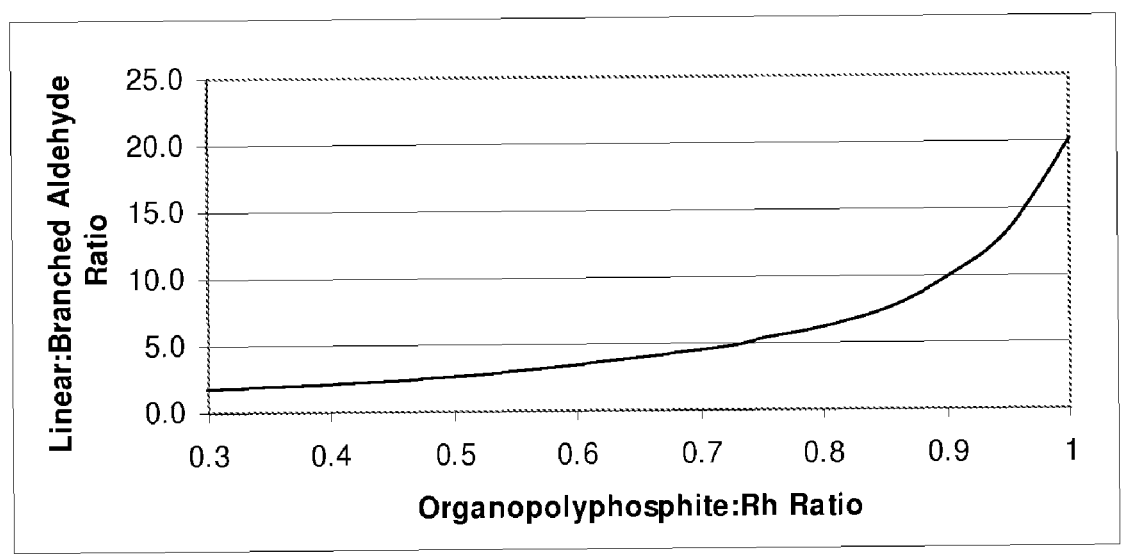
FIG. 2 illustrates a plot of linear/branched aldehyde isomer ratio (N/I) versus molar ratio of a typical organopolyphosphite ligand to transition metal, specifically, rhodium (with excess organomonophosphite ligand).

Data for FIG. 2

| Molar Ratio Organopolyphosphite:Rh | Aldehydes N/I Ratio |
| --- | --- |
| 0.3 | 1.7 |
| 0.4 | 2.1 |
| 0.5 | 2.7 |
| 0.6 | 3.4 |
| 0.7 | 4.5 |
| 0.8 | 6.2 |
| 0.9 | 10 |
| 1.0 | 20 |

To reiterate, Equation 3 can be used to calculate $X_{OPP}$ in the mixed-ligand reaction fluid by using the observed isomer ratio; and Equation 3 can be used to calculate the $X_{OPP}$ needed to obtain a target isomer ratio. The difference in $X_{OPP}$ values corresponds to the amount of organopolyphosphite that needs to be added or removed. A representative example of this relationship is seen in FIG. 2. For example, if the target N/I isomer ratio is 15 and the observed is 5, then the organopolyphosphite:Rh ratio should be moved from about 0.74 to 0.98. Since the moles of transition metal (e.g., Rh) are known (or readily measured), the moles of organopolyphosphite to be added are easily determined.

In practice with laboratory-scale equipment and a low concentration of organopolyphosphite ligand, it is frequently difficult to prevent air oxidation during initiation of the system and any initial charge of organopolyphosphite is often nearly exhausted within an hour. The desired aldehyde isomer ratio is quickly re-established, however, by using the above relationship to calculate the needed organopolyphosphite ligand to be added. For cost effectiveness, the reaction can be initiated using the less expensive organomonophosphite ligand and then the organopolyphosphite ligand can be added to the desired ratio relative to transition metal.

The invention will be further clarified by a consideration of the following examples, which are intended to be purely exemplary of the use of the invention. Other embodiments of the invention will be apparent to those skilled in the art from a consideration of this specification or practice of the invention as disclosed herein.

In the examples that follow, gas flow rates are reported in standard liters per hour (SLH). The hydroformylation reaction rate is reported as moles of aldehyde produced per liter of reaction fluid volume per hour (gmole/l/hr). The purities of propylene and syn gas feeds (1:1 CO:$H_2$ unless otherwise stated) are greater than 99.8 percent.

EXAMPLES

General Procedure for Hydroformylation Process

The hydroformylation process is conducted in a glass pressure reactor operating in a continuous mode. The reactor consists of a three ounce pressure bottle partially submersed in an oil bath with a glass front for viewing. After purging the system with nitrogen, about 20-30 mL of a freshly prepared rhodium catalyst precursor solution is charged to the reactor with a syringe. The catalyst precursor solution contains between 100 and 200 ppm rhodium (introduced as rhodium dicarbonyl acetylacetonate), ligand, and tetraglyme as solvent. After sealing the reactor, the system is purged with nitrogen and the oil bath is heated to furnish the desired hydroformylation reaction temperature. The hydroformylation reaction is conducted at a total pressure of 150 to 160 psig (1034 to 1103 kPa) and at a temperature ranging from 80 to 100° C. A feed comprising nitrogen, syngas, and propylene is started. The flows of the feed gases ($H_2$, CO, propylene, $N_2$) are controlled individually with mass flow meters and the feed gases are dispersed in the catalyst precursor solution via fritted metal spargers. The partial pressures of $N_2$, $H_2$, CO, propylene, and aldehyde products are determined by analyzing the vent stream by GC analysis and Dalton's Law. The unreacted portion of the feed gases is stripped out with butyraldehydes products by the nitrogen flow to maintain substantially constant liquid level. Flows and feed gas partial pressures are selected to obtain hydroformylation reaction rates, as close as possible, to 1 gram-moles aldehyde per liter reaction fluid per hour. The outlet gas is analyzed continuously by GC. Samples of the reaction fluid are withdrawn (via syringe) for $^{31}P$ NMR, Rh, and/or HPLC analyses to confirm catalyst composition and feed purity, and to determine the rate of decomposition of the ligands as a function of time under the reaction conditions. In practice, it is often observed that the system takes about one day to arrive at steady state conditions due to removing trace air from feed lines and reaching thermal equilibration of oil baths; so ligand decomposition studies are only initiated after steady state operations are achieved. This equipment also allows generating hydroformylation rates as a function of reaction temperature, CO and $H_2$ partial pressures, and Rh content.

The reaction system is initiated with the rhodium-organomonophosphite catalyst to establish a preliminary steady state operation and then the N/I isomer ratio is adjusted to the desired target ratio by adding the organopolyphosphite ligand. The organopolyphosphite ligand is then continuously added at the same rate that it decomposes which maintains the target N/I isomer ratio. The rate of ligand decomposition is readily measured beforehand and/or verified during operation by removing catalyst solution samples periodically and analyzing by $^{31}P$ NMR or HPLC. Verification may be required depending on changes in feed purity, buildup of impurities, and process interruptions. Periodic addition of the organomonophosphite may also be required to maintain its molar concentration above super-stoichiometric (>2:1) relative to transition metal. The amount of excess organomonophosphite has little, if any, impact on reactivity or product isomer ratio; so it is generally preferred to keep the molar ratio of organomonophosphite:metal above 5:1.

Control Example 1

Using the general process procedure described hereinabove, a hydroformylation reactor is loaded with a catalyst comprising rhodium (115 ppm, as rhodium dicarbonyl acetylacetonate) and tris(2,4-di-tert-butylphenyl) phosphite (0.72 weight percent in reaction fluid comprising tetraglyme) for a Ligand/Rh molar ratio of 10. $H_2$ and CO partial pressures are maintained at 30 psi (207 kPa) each (the remainder being $N_2$ and propylene). Propylene flow is sufficient to give a hydroformylation rate of 1 gmol/l/hr ($Rate_{(mono)}$). The aldehyde product is analyzed every 4 hours as described above. The N/I isomer ratio is calculated over a running 5 day average (i.e., average of previous 5 days) for nearly one month with the results shown in Table 2.

TABLE 2

Control using Organomonophosphite Ligand

| Day | N/I 5 day average |
|---|---|
| 5 | 0.86 |
| 10 | 0.87 |
| 15 | 0.89 |
| 20 | 0.87 |
| 25 | 0.88 |

Table 2 demonstrates the performance of a Rh-organomonophosphite ligand complex catalyst system, in the absence of organopolyphosphite ligand. Under the operating conditions, an N/I isomer ratio of approximately 0.9 ($N_{mono}$) and an acceptable rate of reaction are obtained. The rate of decomposition of the organomonophosphite is estimated by measuring the concentration of free ligand (via HPLC) as a function of time.

Control Example 2

Following the general process procedure hereinabove, a reactor is charged with rhodium (100 ppm) and organopolyphosphite Ligand D hereinabove (0.24 wt percent in the reaction fluid) for a Ligand/Rh molar ratio of 3:1. The $H_2$ and CO partial pressures are maintained at 30 psi (207 kPa) each (the remainder being $N_2$ and propylene). From a previous study of hydroformylation reaction rate versus CO partial pressure, it is found that 30 psi (207 kPa) CO partial pressure falls within the negative order region of the hydroformylation rate curve (Refer to FIG. 1). Under reaction conditions, the average hydroformylation rate is 0.9 gmol/l/hr ($Rate_{(poly)}$), measured as a daily running average. The aldehyde product is analyzed every 4 hours as described above. The N/I isomer ratio is calculated over a running daily average for 8 days with the results shown in Table 3.

TABLE 3

Control Using Organopolyphosphite Ligand

| Day | N/I Daily average |
|---|---|
| 1 | 22 |
| 4 | 38 |
| 5 | 40 |
| 6 | 39 |
| 7 | 38 |
| 8 | 34 |

Table 3 demonstrates the performance of the Rh-organopolyphosphite ligand catalyst system which gives an N/I isomer ratio of approximately 35 ($N_{poly}$) under the reaction conditions.

This control experiment can also be used to establish the hydroformylation reaction rate versus CO partial pressure curve by changing the CO partial pressure (keeping all other parameters constant) and noting changes in the observed hydroformylation rate. The rate of decomposition of the organopolyphosphite is estimated by measuring the concentration of free ligand (via HPLC) over time.

Example 1

A hydroformylation process is conducted in accordance with the general procedure described hereinabove. A target N/I isomer ratio is set at 4.0 and Equation 3 and FIG. 2 are used to estimate an initial molar ratio ($X_{opp}$) of organopolyphosphite ligand:Rh of 0.7/1. The catalyst solution comprises rhodium (115 ppm), tris(2,4-di-tert-butylphenyl)phosphite (0.7 wt percent based on reaction fluid) for an organomonophosphite:Rh molar ratio of 10:1, and organopolyphosphite Ligand D (0.07 wt percent based on reaction fluid) for an initial molar ratio of Ligand D:Rh of 0.8/1 ($X_{opp}$) (which is slightly high to allow for some oxidation) in tetraglyme. Using Ligand D and propylene, CO partial pressures in the negative order region of the hydroformylation rate curve are pre-determined per the method described in WO-2006-020287 and summarized hereinabove, resulting in FIG. 1. A pressure of 30 psi (207 kPa) is determined to lie in the negative order region of the rate curve and is used in this experiment. $H_2$ and CO partial pressures are maintained at approximately 30 psi each (207 kPa), the CO partial pressure being within the prescribed negative order regime; the balance being $N_2$, propylene, and aldehyde product. The aldehyde product is analyzed on a continuous basis as described above (approximately every 4 hours). Additional aliquots of organopolyphosphite ligand are added (dissolved in tetrahydrofuran, THF) as needed to replenish degraded ligand and maintain the N/I isomer ratio. The aliquots comprise 0.009 equivalents Ligand D/day on average. The average N/I isomer ratio is calculated on a 5 day running average for nearly one month and presented in Table 4.

TABLE 4

Example Using Mixed-Ligand System

| Day | N/I 5 day average |
|---|---|
| 5 | 3.3 |
| 10 | 3.5 |
| 15 | 3.6 |
| 20 | 4.1 |
| 25 | 3.9 |
| 30 | 3.8 |
| 35 | 3.8 |
| 40 | 4.1 |
| 45 | 4.7 |
| 50 | 4.7 |
| 55 | 4.3 |
| 60 | 4.4 |
| 65 | 4.7 |

From Table 4 it is seen that while the initial N/I isomer ratio is somewhat low, the mixed-ligand system is readily brought to the target N/I isomer ratio of 4 and remains stable out to 65 days. The target N/I isomer ratio of 4 is situated well between the isomer ratio $N_{mono}$ of 0.9 and the $N_{poly}$ of 35. Other target ratios can be dialed in analogously. Moreover, the target ratio is achieved without changing the CO partial pressure, which lies in the negative order region of the rate curve and steady at 30 psi (207 kPa) (wherein the organopolyphosphite ligand is stabilized against unacceptable hydrolytic degradation). Furthermore, the quantity of ligands employed in the subject invention lies well below the excess levels required in organophosphine ligand-based hydroformylation processes.

The invention claimed is:

1. A hydroformylation process for continuous production of a mixture of aldehyde products with control over a normal/branched (N/I) isomer ratio of the product aldehydes; the process comprising the steps of: contacting under continuous reaction conditions in a hydroformylation reaction fluid, one or more olefinically-unsaturated compounds, carbon monoxide, and hydrogen in the presence of a mixture of an organopolyphosphite ligand and an organomonophosphite ligand, at least one of said ligands being bonded to a transition metal to form a transition metal-ligand complex hydroformylation catalyst; the organopolyphosphite ligand comprising a plurality of phosphorus (III) atoms each bonded to three hydrocarbyloxy radicals, any non-bridging species of which consists essentially of an aryloxy radical (substituted or unsubstituted); the contacting further conducted in a manner comprising:
    (a) at a sub-stoichiometric molar ratio of organopolyphosphite ligand to transition metal such that said molar ratio is greater than 0 but less than 1.0/1;
    (b) at a super-stoichiometric molar ratio of organomonophosphite ligand to transition metal such that said molar ratio is greater than 2/1;
    (c) at a carbon monoxide partial pressure in a negative order region of a hydroformylation rate curve wherein rate of reaction decreases as carbon monoxide partial pressure increases, and wherein rate of reaction increases as carbon monoxide partial pressure decreases, the rate curve being measured on an identical hydroformylation process in the presence of the organopolyphosphite ligand but not the organomonophosphite ligand; and
    (d) varying the molar ratio of organopolyphosphite ligand to transition metal within the aforementioned sub-stoichiometric range while maintaining the molar ratio of organomonophosphite ligand to transition metal in the aforementioned super-stoichiometric range, so as to control continuously the normal/branched isomer ratio of the aldehyde products.

2. The process of claim 1 wherein the normal/branched isomer ratio varies continuously from 1/1 to 100/1.

3. The process of claim 1 wherein the molar ratio of organopolyphosphite ligand to transition metal is decreased by reacting the organopolyphosphite ligand with water in the reaction fluid, or by addition of water to the reaction fluid, or by reacting the organopolyphosphite ligand with an oxidant selected from oxygen, air, hydrogen peroxide, and organic hydroperoxides.

4. The process of claim 1 wherein the molar ratio of organopolyphosphite ligand to transition metal is decreased by degrading the organopolyphosphite through pH or temperature means.

5. The process of claim 1 wherein the molar ratio of organopolyphosphite ligand to transition metal is increased by adding organopolyphosphite ligand to the reaction fluid.

6. The process of claim 1 wherein the organopolyphosphite ligand is represented by the following formula:

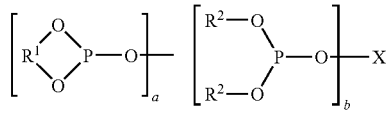

wherein X represents a substituted or unsubstituted n-valent organic bridging radical containing from 2 to 40 carbon atoms, each $R^1$ is the same or different and represents a divalent arylene radical containing from 6 to 40 carbon atoms, and each $R^2$ is the same or different and represents a substituted or unsubstituted monovalent aryl radical containing from 6 to 24 carbon atoms; a and b can be the same or different and each has a value of 0 to 6, with the proviso that the sum of a+b is 2 to 6 and n equals a+b.

7. The process of claim 6 wherein the organopolyphosphite ligand is selected from the following group of formulas:

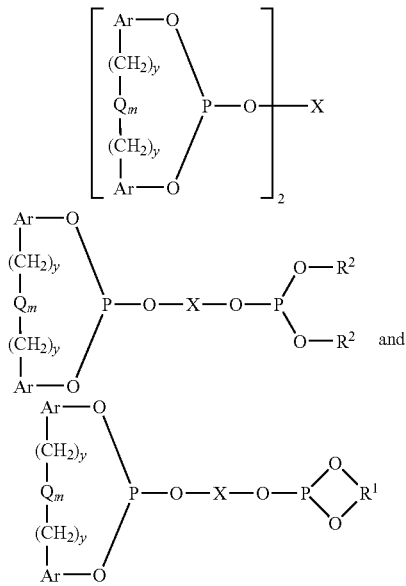

wherein X represents a substituted or unsubstituted n-valent organic bridging radical containing from 2 to 40 carbon atoms, each $R^1$ is the same or different and represents a divalent arylene radical containing from 6 to 40 carbon atoms, and each $R^2$ is the same or different and represents a substituted or unsubstituted monovalent aryl radical containing from 6 to 24 carbon atoms; wherein each y is the same or different and is a value of 0 or 1; Q represents a divalent bridging group selected from $—C(R^3)_2—$, $—O—$, $—S—$, $—NR^4—$, $—Si(R^5)_2—$ and $—CO—$, wherein each $R^3$ is the same or different and represents hydrogen, a $C_{1-12}$ alkyl radical, phenyl, tolyl, or anisyl, $R^4$ represents hydrogen or a substituted or unsubstituted monovalent hydrocarbon radical; each $R^5$ is the same or different and represents hydrogen or a $C_{1-10}$ alkyl radical; and m is a value of 0 or 1.

8. The process of claim 1 wherein the organopolyphosphite ligand is selected from the following group:
    6,6'-[[4,4'-bis(1,1-dimethylethyl)-[1,1'-binaphthyl]-2,2'-diyl]bis(oxy)]bis-dibenzo[d,f][1,3,2]-dioxaphosphepin having the formula:

Ligand A

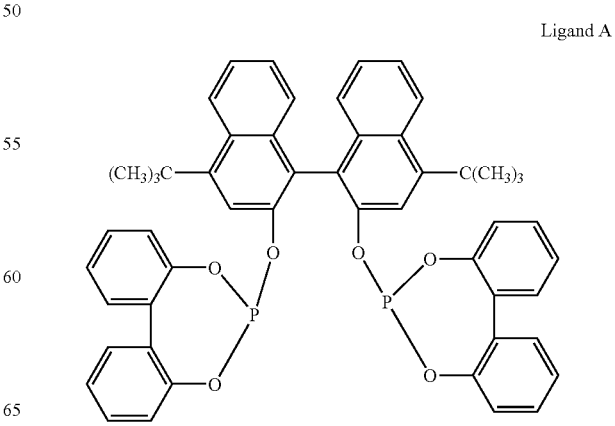

6,6'-[[3,3'-bis(1,1-dimethylethyl)-5,5'-dimethoxy-[1,1'-biphenyl]-2,2'-diyl]bis(oxy)]bis-dibenzo[d,f][1,3,2]dioxaphosphepin having the formula:

Ligand B

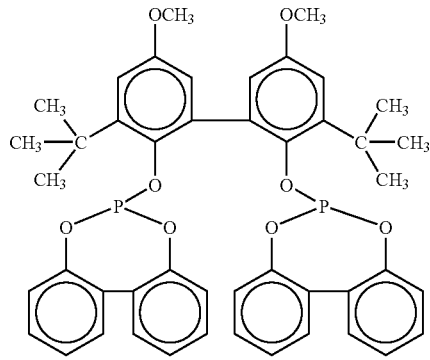

6,6'-[[3,3',5,5'-tetrakis(1,1-dimethylethyl)-[1,1'-biphenyl]-2,2'-diyl]bis(oxy)]bis-dibenzo[d,f][1,3,2]-dioxaphosphepin having the formula:

Ligand D

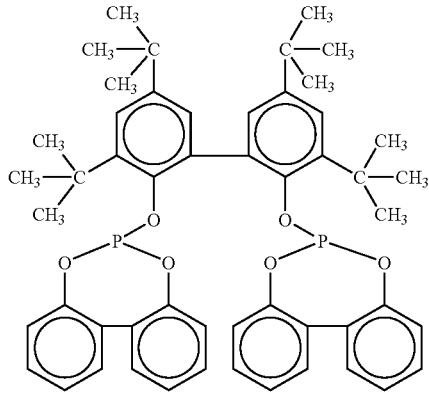

(2R,4R)-di[2,2'-(3,3',5,5'-tetrakis-tert-amyl-1,1'-biphenyl)]-2,4-pentyldiphosphite having the formula:

Ligand E

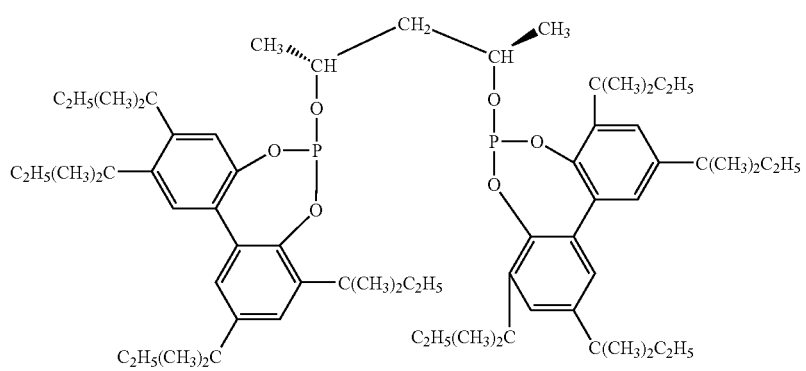

6,6'-[[3,3',5,5'-tetrakis(1,1-dimethylpropyl)-[1,1'-biphenyl]-2,2'-diyl]bis(oxy)]bis-dibenzo[d,f][1,3,2]dioxaphosphepin having the formula:

(2R,4R)-di[2,2'-(3,3',5,5'-tetrakis-tert-butyl-1,1'-biphenyl)]-2,4-pentyldiphosphite having the formula:

Ligand C

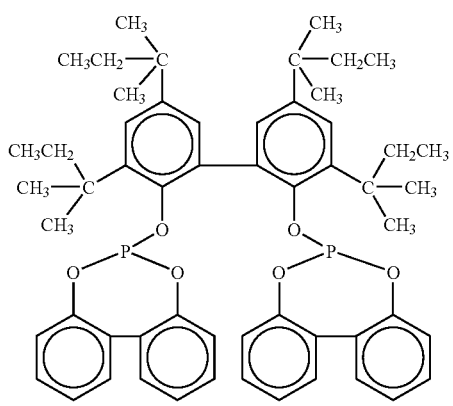

Ligand F

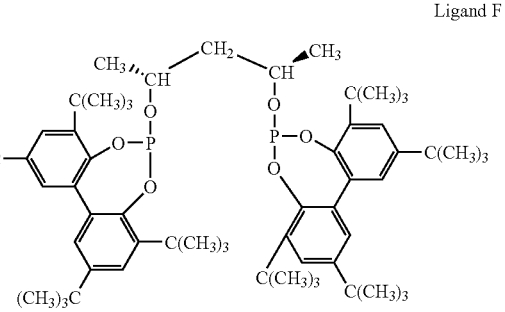

(2R,4R)-di[2,2'-(3,3'-di-amyl-5,5'-dimethoxy-1,1'-biphenyl)]-2,4-pentyldiphosphite having the formula:

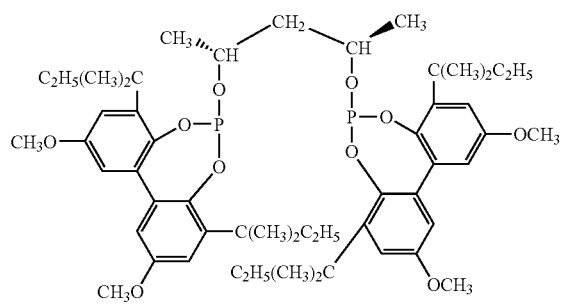

Ligand G (2R,4R)-di[2,2'-(3,3'-di-tert-butyl-5,5'-dimethyl-1,1'-biphenyl)]-2,4-pentyldiphosphite having the formula:

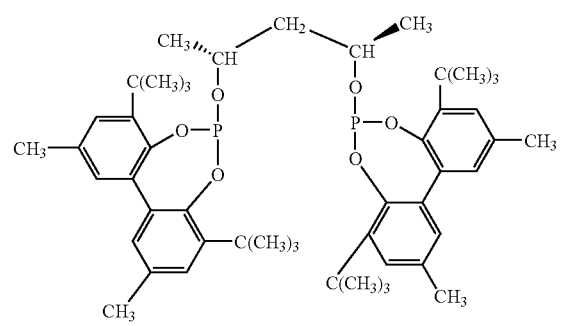

Ligand H (2R,4R)-di[2,2'-(3,3'-di-tert-butyl-5,5'-diethoxy-1,1'-biphenyl)]-2,4-pentyldiphosphite having the formula:

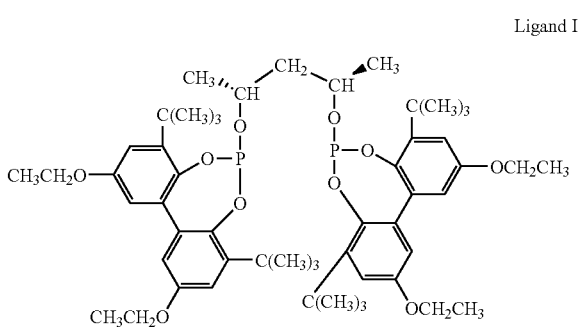

Ligand I (2R,4R)-di[2,2'-(3,3'-di-tert-butyl-5,5'-diethyl-1,1'-biphenyl)]-2,4-pentyldiphosphite having the formula:

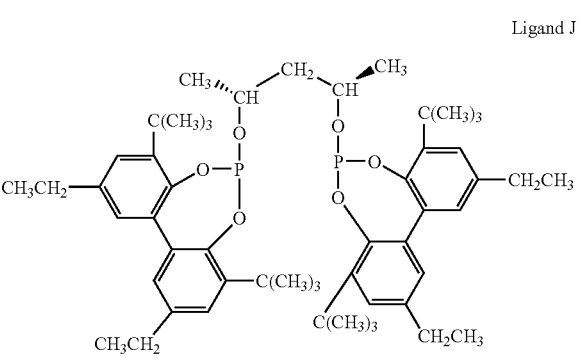

Ligand J (2R,4R)-di[2,2'-(3,3'-di-tert-butyl-5,5'-dimethoxy-1,1'-biphenyl)]-2,4-pentyldiphosphite having the formula:

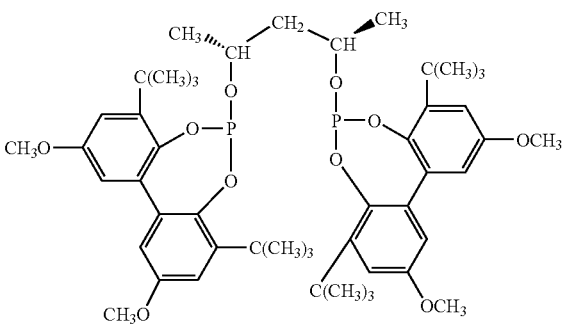

Ligand K

6-[[2'-[(4,6-bis(1,1-dimethylethyl)-1,3,2-benzodioxaphosphol-2-yl)oxy]-3,3'-bis(1,1-dimethylethyl)-5,5'-dimethoxy[1,1'-biphenyl]-2-yl]oxy]-4,8-bis(1,1-dimethylethyl)-2,10-dimethoxydibenzo[d,f][1,3,2]dioxaphosphepin having the formula:
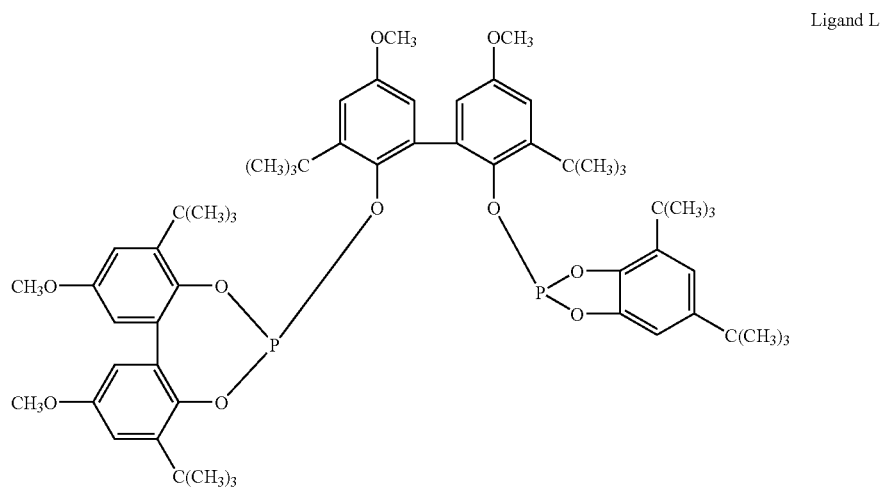
Ligand L
6-[[2'-[1,3,2-benzodioxaphosphol-2-yl)oxy]-3,3'-bis(1,1-dimethylethyl)-5,5'-dimethoxy[1,1'-biphenyl]-2-yl]oxyl-4,8-bis(1,1-dimethylethyl)-2,10-dimethoxy-dibenzo[d,f][1,3,2]dioxaphosphepin having the formula:
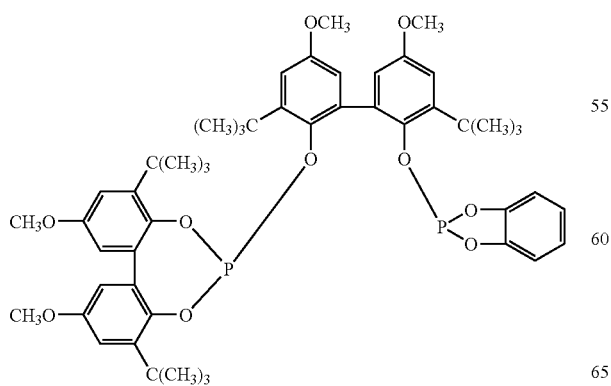
Ligand M 2'-[[4,8-bis(1,1-dimethylethyl)-2,10-dimethoxydibenzo[d,f][1,3,2]-dioxaphosphepin-6-yl]oxy]-3,3'-bis(1,1-dimethylethyl)-5,5'-dimethoxy[1,1'-biphenyl]-2-yl bis(4-hexylphenyl)ester of phosphorous acid having the formula:

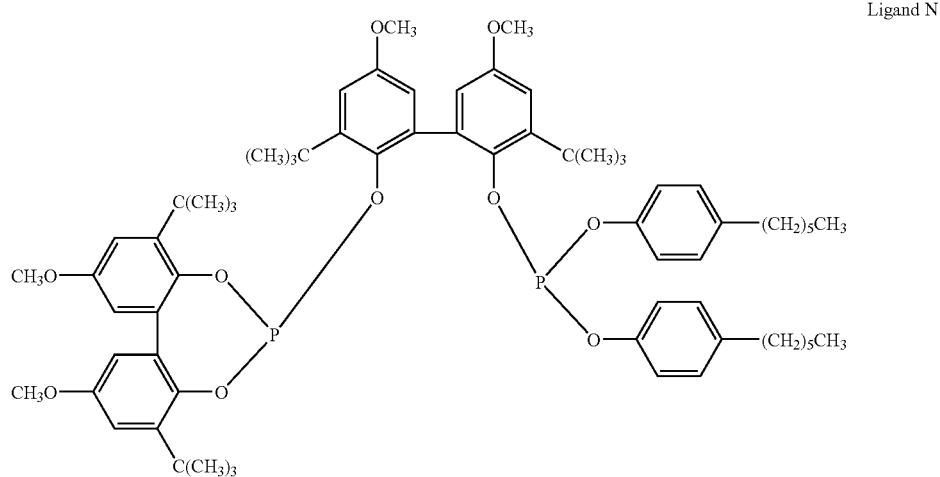

Ligand N

2-[[2-[[4,8,-bis(1,1-dimethylethyl), 2,10-dimethoxy-dibenzo-[d,f][1,3,2]dioxophosphepin-6-yl]oxyl-3-(1,1-dimethylethyl)-5-methoxyphenyl]methyl]-4-methoxy, 6-(1,1-dimethylethyl)phenyl diphenyl ester of phosphorous acid having the formula:

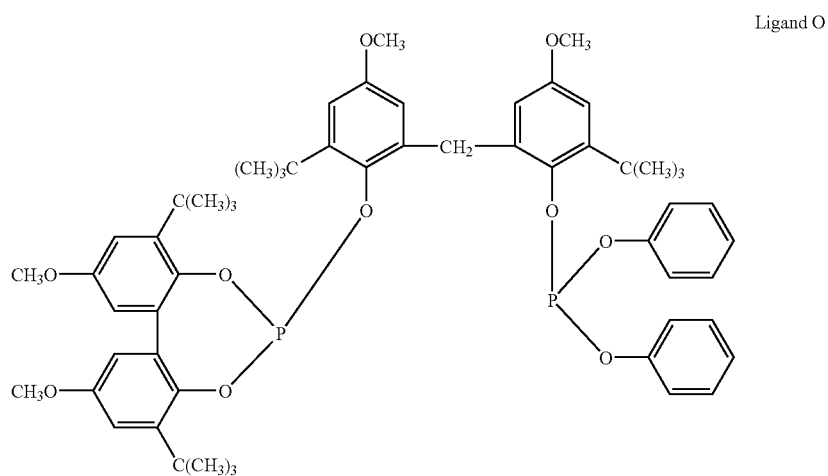

Ligand O 3-methoxy-1,3-cyclohexamethylene tetrakis[3,6-bis(1,1-dimethylethyl)-2-naphthalenyl]ester of phosphorous acid having the formula:

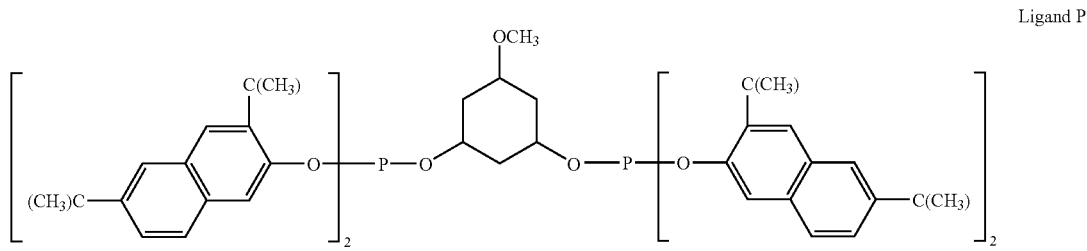

Ligand P 2,5-bis(1,1-dimethylethyl)-1,4-phenylene tetrakis[2,4-bis(1,1-dimethylethyl)phenyl]ester of phosphorous acid having the formula:

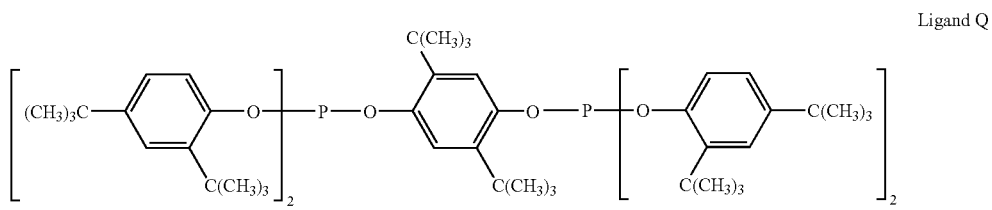

Ligand Q methylenedi-2,1-phenylene tetrakis[2,4-bis(1,1-dimethylethyl)phenyl]ester of phosphorous acid having the formula:

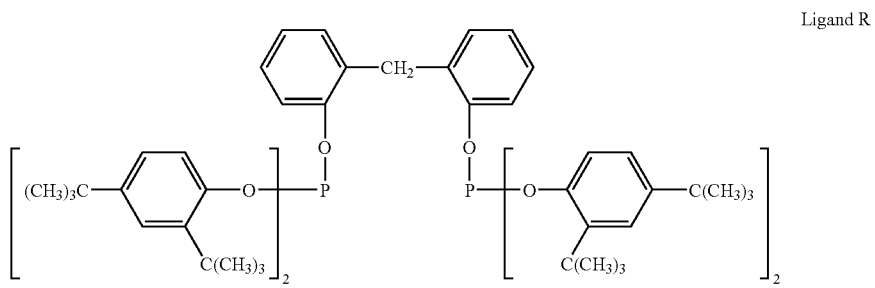

Ligand R

[1,1'-biphenyl]-2,2'-diyl tetrakis[2-(1,1-dimethylethyl)-4-methoxyphenyl]ester of phosphorous acid having the formula:

Ligand S

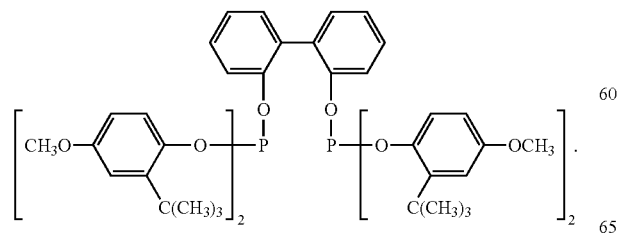

9. The process of claim 1 wherein the organomonophosphite ligand is represented by any one of the following formulas:

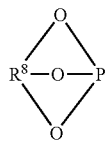

wherein $R^8$ represents a substituted or unsubstituted trivalent hydrocarbon radical containing from 4 to 40 carbon atoms;

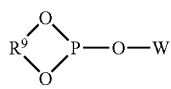

wherein $R^9$ represents a substituted or unsubstituted divalent hydrocarbon radical containing from 4 to 40 carbon atoms, and W represents a substituted or unsubstituted monovalent hydrocarbon radical containing from 1 to 18 carbon atoms; or

wherein each $R^{13}$ is the same or different and is a substituted or unsubstituted monovalent hydrocarbon radical having from 1 to 24 carbon atoms.

10. The process of claim 1 wherein the organomonophosphite is represented by the following formula:

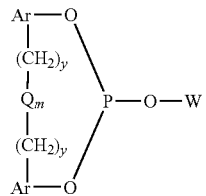

wherein W represents a substituted or unsubstituted monovalent hydrocarbon radical containing from 1 to 18 carbon atoms; each Ar is the same or different and represents a substituted or unsubstituted aryl radical; each y is the same or different and is a value of 0 or 1; Q represents a divalent bridging group selected from —$C(R^{10})_2$—, —O—, —S—, —$NR^{11}$—, —$Si(R^{12})_2$— and —CO, wherein each $R^{10}$ is the same or different and represents hydrogen, an alkyl radical having from 1 to 10 carbon atoms, phenyl, tolyl, or anisyl, $R^{11}$ represents hydrogen or an alkyl radical of from 1 to 10 carbon atoms, each $R^{12}$ is the same or different and represents hydrogen or an alkyl radical having from 1 to about 10 carbon atoms, and m is a value of 0 or 1.

11. The process of claim 1 wherein the organopolyphosphite ligand is 6,6'-[[3,3',5,5'-tetrakis(1,1-dimethylethyl)-1,1'-biphenyl]-2,2'-diyl]bis(oxy)]bis-dibenzo[d,f][1,3,2-dioxaphosphepin, and the organomonophosphite ligand is tris(2,4-di-tert-butylphenyl) phosphite.

12. The process of claim 1 wherein concentration of the transition metal is greater than about 1 part per million (ppm) and less than about 120 ppm, based on the weight of the hydroformylation reaction fluid.

13. The process of claim 1 wherein the process temperature is greater than about −25° C. and less than about 200° C.

14. The process of claim 1 wherein the total gas pressure comprising carbon monoxide, hydrogen, and olefinic reactant(s) ranges from greater than about 25 psia (173 kPa) and less than about 2,000 psia (6,895 kPa).

15. The process of claim 1 wherein the carbon monoxide partial pressure ranges from about 15 psia (103.4 kPa) to about 100 psia (689 kPa).

16. The process of claim 1 wherein the olefin is an achiral alpha-olefin having from 2 to 30 carbon atoms or an achiral internal olefin having from 4 to 20 carbon atoms.

17. The process of claim 1 wherein carbon monoxide and hydrogen are present in quantities that provide an $H_2$:CO molar ratio ranging from 1:10 to 100:1.

18. The process of claim 1 wherein the transition metal is a Group VIII metal selected from rhodium, cobalt, iridium, ruthenium, and mixtures thereof.

19. The process of claim 1 wherein the super-stoichiometric ratio of organomonophosphite ligand to transition metal ranges from 2/1 to about 100/1, and wherein the sub-stoichiometric ratio of organopolyphosphite ligand to transition metal ranges from about 0.01/1 to less than 1.0/1.

20. The process of claim 1 wherein the olefin is propylene, the organopolyphosphite ligand is 6,6'[[3,3',5,5'-tetrakis(1,1-dimethylethyl)-1,1'-biphenyl]-2,2'-diyl]bis(oxy)]bis-dibenzo[d,f][1,3,2-dioxaphosphepin, the organomonophosphite ligand is tris(2,4-di-tert-butylphenyl) phosphite, and the normal/branched aldehyde product isomer ratio ranges from 2/1 to 75/1.

* * * * *